(12) United States Patent
Wang et al.

(10) Patent No.: US 8,900,835 B2
(45) Date of Patent: Dec. 2, 2014

(54) **ENGINEERING OF THERMOTOLERANT *BACILLUS COAGULANS* FOR PRODUCTION OF D(–)-LACTIC ACID**

(75) Inventors: Qingzhao Wang, Gainesville, FL (US); Keelnatham T. Shanmugam, Gainesville, FL (US); Lonnie O. Ingram, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/301,836

(22) Filed: Nov. 22, 2011

(65) Prior Publication Data

US 2012/0129231 A1   May 24, 2012

Related U.S. Application Data

(60) Provisional application No. 61/416,002, filed on Nov. 22, 2010.

(51) Int. Cl.
*C12P 7/56* (2006.01)
*C12N 1/20* (2006.01)
*C12N 9/04* (2006.01)
*C12N 9/10* (2006.01)

(52) U.S. Cl.
CPC ............... *C12P 7/56* (2013.01); *C12N 9/0006* (2013.01); *C12N 9/1022* (2013.01)
USPC ........................................ 435/139; 435/252.3

(58) Field of Classification Search
CPC ...... C12N 1/16; C12N 9/0006; C12N 15/625; C12N 15/8216; C12N 15/87; C12N 2310/321; C12N 2510/00; C12N 5/0634; C12N 9/1096; C12N 9/90; C12N 11/08; C12N 15/115; C12N 15/52; C12N 15/67; C12N 9/88; C12N 15/07; C12P 7/56
USPC .............................................. 435/139, 252.3
See application file for complete search history.

(56) References Cited

U.S. PATENT DOCUMENTS

| | | | |
|---|---|---|---|
| 6,197,559 B1 * | 3/2001 | Moriya et al. ............... | 435/110 |
| 7,098,009 B2 | 8/2006 | Shanmugam et al. | |
| 2006/0040279 A1 | 2/2006 | Feesche et al. | |
| 2008/0293101 A1 * | 11/2008 | Peters et al. ............... | 435/69.1 |
| 2009/0197314 A1 | 8/2009 | Atkinson et al. | |

FOREIGN PATENT DOCUMENTS

| | | |
|---|---|---|
| CN | 101544992 | 9/2009 |
| DE | 102 42 433 | 3/2004 |

OTHER PUBLICATIONS

Wang et al. Metabolic Flux control at the pyruvate node in an anaerobic *E. coli* starin with an active pyruvate dehydrogenase. Apr. 2010, Applied and Environ. Microbiol. 76 (7), 2107-2114.*
Sen et al., Developmens in ditected evolution for improving enzyme functions. Appl. Biochem. Biotechnol., 2007, 143:2, 212-223.*
Chica et al., Semi-ratiinal approaches to engineering enzyme activity: combining the benefivts of directed evolution and rational design. Current opinion in Biotech. 2005, 16: 378-384.*
Romero, S. et al. "Metabolic Engineering of *Bacillus subtilis* for Ethanol Production: Lactate Dehydrogenase Plays a Key Role in Fermentative Metabolism" *Applied and Environmental Microbiology*, Aug. 2007, pp. 5190-5198, vol. 73, No. 16.
Su, Y. et al. "Physiological and fermentation properties of *Bacillus coagulans* and a mutant lacking fermentative lactate dehydrogenase activity" *The Journal of Industrial Microbiology and Biotechnology*, 2011, pp. 441-450, vol. 38.
Wang, Q. et al. "Construction and characterization of an *ldh* deletion mutant of *Bacillus coagulans*" *A special conference of the Society for industrial Microbiology, 32nd Symposium on Biotechnology for Fuels and Chemicals*, Apr. 19, 2010, Section 1-10, pp. 1-2.
Shanmugam, K. T. et al. "Engineering Thermotolerant Biocatalysts for Biomass Conversion to Products" *Technical Report (final)*, May 20, 2010, DOE Contract No. FG36-04G014019.
Zhang, Z. et al. "One-step production of lactate from cellulose as the sole carbon source without any other organic nutrient by recombinant cellulolytic *Bacillus subtilis*" *Metabolic Engineering*, 2011, pp. 364-372, vol. 13.
Wang, Q. et al. "Metabolic Engineering of thermotolerant, acidophilic *Bacillus coagulans* for production of D(–)-lactic acid" *In: SIM Annual Meeting and Exhibition*, Jul. 26, 2011, Section S123, pp. 1.
Wang, Q. et al. "Evolution of D-lactate dehydrogenase activity from glycerol dehydrogenase and its utility for D-lactate production from lignocellulose" *PNAS*, Nov. 11, 2011, pp. 18920-18925, vol. 108 No. 47.
Datta, R. et al. "Lactic acid: recent advances in products, processes and technologies—a review" *Journal of Chemical Technology and Biotechnology*, 2006, pp. 1119-1129, vol. 81.
Grabar T.B. et al. "Methylglyoxal bypass identified as source of chiral contamination in L(+) and D(–)-lactate fermentations by recombinant *Escherichia coli*" *Biotechnology Letters*, 2006, pp. 1527-1535, vol. 28.
Hofvendahl, K. et al. "Factors affecting the fermentative lactic acid production from renewable resources" *Enzyme and Microbial Technology*, 2000, pp. 87-107, vol. 26.
Kim, Y. et al. "Construction of an *Escherichia coli* K-12 mutant for homoethanologenic fermentation of glucose or xylose without foreign genes" *Applied and Environmental Microbiology*, 2007, pp. 1766-1771, vol. 73.

(Continued)

*Primary Examiner* — Tekchand Saidha
(74) *Attorney, Agent, or Firm* — Saliwanchik, Lloyd & Eisenschenk

(57) ABSTRACT

Genetically modified microorganisms having the ability to produce D(–)-lactic acid at temperatures between 30° C. and 55° C. are provided. In various embodiments, the microorganisms may have the chromosomal lactate dehydrogenase (ldh) gene and/or the chromosomal acetolactate synthase (alsS) gene inactivated. Exemplary microorganisms for use in the disclosed methods are *Bacillus* spp., such as *Bacillus coagulans*.

24 Claims, 7 Drawing Sheets

(56) References Cited

OTHER PUBLICATIONS

Kim, Y. et al. "Dihydrolipoamide dehydrogenase mutation alters the NADH sensitivity of pyruvate dehydrogenase complex of *Escherichia coli* K-12" *Journal of Bacteriology*, 2008, pp. 3851-3858, vol. 190, No. 11.

Okano, K. et al. "Improved production of homo-D-lactic acid via xylose fermentation by introduction of xylose assimilation genes and redirection of the phosphoketolase pathway to the pentose phosphate pathway in L-Lactate dehydrogenase gene-deficient *Lactobacillus plantarum*" *Applied and Environmental Microbiology*, 2009, pp. 7858-7861, vol. 75, No. 24.

Ou, M. et al. "L: (+)-Lactic acid production from non-food carbohydrates by thermotolerant *Bacillus coagulans*" *The Journal of Industrial Microbiology and Biotechnology*, 2011, pp. 599-605, vol. 38.

Patel, M.A. et al. "Isolation and characterization of acid-tolerant, thermophilic bacteria for effective fermentation of biomass-derived sugars to lactic acid" *Applied and Environmental Microbiology*, 2006, pp. 3228-3235, vol. 72.

Payot, T. et al. "Lactic acid production by *Bacillus coagulans*—Kinetic studies and optimization of culture medium for batch and continuous fermentations" *Enzyme and Microbial Technology*, 1999, pp. 191-199, vol. 24.

Tanaka, K. et al. "Two different pathways for D-xylose metabolism and the effect of xylose concentration on the yield coefficient of L-lactate in mixed-acid fermentation by the lactic acid bacterium *Lactococcus lactis* IO-1" *Applied Microbiology and Biotechnology*, 2002, pp. 160-167, vol. 60.

Underwood, S.A. et al. "Genetic changes to optimize carbon partitioning between ethanol and biosynthesis in ethanologenic *Escherichia coli*" *Applied and Environmental Microbiology*, 2002, pp. 6263-6272, vol. 68.

Yanez, R. et at "Production of D(−)-lactic acid from cellulose by simultaneous saccharification and fermentation using *Lactobacillus coryniformis* subsp. *torquens*" *Biotechnology Letters*, 2003, pp. 1161-1164, vol. 25.

Zhou S. et al. "Functional replacement of the *Escherichia coli* D-(−)-lactate dehydrogenase gene (IdhA) with the L-(+)-lactate dehydrogenase gene (IdhL) from *Pediococcus acidilactici*" *Applied and Environmental Microbiology*, 2003, pp. 2237-2244, vol. 69.

Written Opinion in International Application No. PCT/US2011/061807, Jul. 23, 2012, pp. 1-4.

Baek-Rock, O. et al. "Optimization of Culture Conditions for 1,3-Propanediol Production from Glycerol Using a Mutant Strain of *Klebsiella pneumoniae*" *Appl Biochem Biotechnol*, 2012, pp. 127-137, vol. 166.

* cited by examiner

ENGINEERING OF THERMOTOLERANT *BACILLUS COAGULANS* FOR PRODUCTION OF D(−)-LACTIC ACID

CROSS REFERENCE TO RELATED APPLICATION

This application claims the benefit of U.S. Provisional Patent Application Ser. No. 61/416,002, filed Nov. 22, 2010, the disclosure of which is hereby incorporated by reference in its entirety, including all figures, tables and nucleic acid sequences. The Sequence Listing for this application is labeled "Seq-List.txt" which was created on Nov. 21, 2011 and is 39 KB. The entire contents of the sequence listing is incorporated herein by reference in its entirety.

GOVERNMENTAL SUPPORT

This invention was made with government support under Department of Energy grant number DE-FG36-04GO14019. The government has certain rights in the invention.

BACKGROUND OF THE INVENTION

Petroleum serves not only as the primary source of fuel but also as the raw material for production of various polymers used by the plastics industry. The finite nature of the petroleum reserves and the negative environmental impact from the use of petroleum has shifted attention towards alternate, renewable source of fuels and chemicals as replacements for petroleum (23). Fermentation of carbohydrates has been shown to produce various short chain hydroxy acids as well as other chemicals that can be polymerized to produce plastics with differing physical and chemical properties. Among these fermentation products, lactic acid stands out as a primary chemical that can be a starting material for manufacture of biodegradable, renewable plastics with minimal environmental impact; $CO_2$ neutral. Fermentation of sugars to lactic acid dates back to pre-historic times and commercial production of lactic acid using pure bacterial cultures started as early as 1895 (3). Although lactic acid is primarily used by food and pharmaceutical industries, lactic acid derived biopolymer production is expected to outstrip these uses provided the cost of production of lactic acid based polymer is comparable to the polymers derived from petrochemicals (8, 14, 18).

Lactic acid is condensed into lactide, purified and polymerized to polylactide (PLA), a thermoplastic (18, 22). By judicial mixing of the D(−)- and L(+)-lactic acid, polymers with various physical and thermochemical properties can be produced. Although lactic acid can be synthesized from petroleum, the product is a mixture of the two isomers and is not suitable for PLA production. Optically pure lactic acid required for PLA production is produced only by microbial fermentation (14). Various lactic acid bacteria, *Lactobacillus*, *Lactococcus*, etc., produce L(+)-lactic acid at high yield and titer from fermentable sugars such as glucose and sucrose (6, 14). Their nutritional requirements are complex and their growth temperature range between 30° C. and 35° C. Microorganisms that produce D(−)-lactic acid as the primary fermentation product has been described and is currently being used by industry (25, 34, 36) (12). Lactic acid fermentation by these microbial biocatalysts is currently conducted at 30-37° C. and raising the growth and fermentation temperature to 50-55° C. is expected to minimize contamination of large scale industrial fermentations (1). In order to reduce the cost of lactic acid production and also to eliminate the use of food carbohydrates as feedstock for lactic acid production, alternate sources of fermentable sugars and microbial biocatalysts are being developed. Lignocellulosic biomass is an attractive source of sugars; glucose, xylose, etc. However, the lactic acid bacteria used by the industry lacks the ability to ferment pentoses efficiently to lactic acid although there are several attempts to improve the xylose fermentation property of these lactic acid bacteria (25, 31).

*Bacillus coagulans* is a sporogenic lactic acid bacterium that grows at 50-55° C. and pH 5.0 and ferments both hexoses and pentoses (10, 27). This bacterium has been shown to produce L(+)-lactic acid at concentrations as high as 180 g/L in fed-batch fermentations from both glucose and xylose and is also an excellent candidate for simultaneous saccharification and fermentation of cellulose to optically pure lactic acid (26). *B. coagulans* is, generally, recalcitrant to genetic engineering and methods for producing pure lactic acid are needed (particularly using genetically engineered microorganisms that do not contain exogenous nucleic acid sequences). One aspect of the invention disclosed herein provides a general method for engineering this genetically recalcitrant bacterium. Using the disclosed method and growth-based selection, the fermentation product of *B. coagulans* strain P4-102B is changed from L(+)-lactic acid to D(−)-lactic acid. The engineered biocatalyst produced about 90 g/L of D(−)-lactic acid in less than 48 hours at 50° C.

BRIEF SUMMARY OF THE INVENTION

Genetically modified microorganisms having the ability to produce D(−)-lactic acid at temperatures between 30° C. and 55° C. are provided. In various embodiments, the microorganisms may have the chromosomal lactate dehydrogenase (ldh) gene and/or the chromosomal acetolactate synthase (alsS) gene inactivated. Exemplary microorganisms for use in the disclosed methods are *Bacillus* spp., such as *Bacillus coagulans*. Microorganisms produced according to the instant disclosure produce D(−)-lactic acid in amounts of at least 60 g/L of culture medium, (e.g., at least 70 g/L, 80 g/L, 90 g/L or 100 g/L). Methods of making and using the disclosed genetically modified microorganisms are also provided.

BRIEF DESCRIPTION OF THE SEQUENCES

Figure 1A:
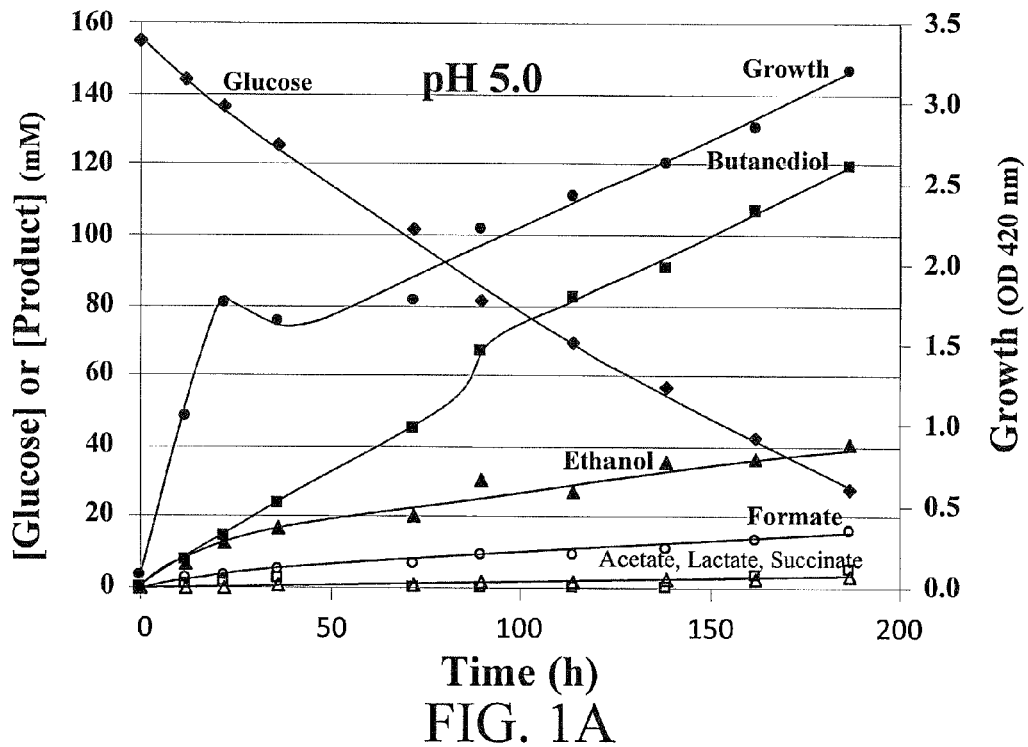
FIGS. 1A-1B. Fermentation profile of *B. coagulans* strain QZ4 (Δldh) at pH 5.0 (FIG. 1A) and pH 7.0 (FIG. 1B). Fermentations were conducted in small fermenters with pH control in LB with glucose. Starting glucose concentration was 30 g/L at pH 5.0 and 50 g/L at pH 7.0.

SEQ ID NO: 1 encodes lactate dehydrogenase gene of *B. coagulans* P4-102B.
SEQ ID NO: 2 encodes acetolactate synthase of *B. coagulans* P4-102B.
SEQ ID NO: 3 encodes pyruvate formate lyase (pfl) of *B. coagulans* P4-102B.

DETAILED DISCLOSURE OF THE INVENTION

One aspect of the subject application provides genetically modified microorganisms having the ability to produce D(−)-lactic acid. In various embodiments of this aspect of the invention, the microorganisms may have the chromosomal lactate dehydrogenase (ldh) gene, chromosomal pyruvate formate lyase (pflB) gene, pyruvate formate lyase activating enzyme (pflA), alpha-acetolactate decarboxylase (alsD) and/or the chromosomal acetolactate synthase (alsS) gene inactivated and the microorganism is a *Bacillus* spp., such as *Bacillus coagulans*. Microorganisms produced according to the instant disclosure produce D(−)-lactic acid in amounts of at least 60 g/L of culture medium, (e.g., at least 70 g/L, 80 g/L, 90 g/L or 100 g/L). In certain aspects of the invention, the chromosomal lactate dehydrogenase (ldh) gene, chromosomal pyruvate formate lyase gene (pflB) and the chromosomal acetolactate synthase (alsS) gene inactivated. Other aspects provide microorganisms in which the chromosomal lactate dehydrogenase (ldh) gene and the chromosomal acetolactate synthase (alsS) gene inactivated. Other aspects of the invention provide for microorganisms having various combinations of inactivated enzymatic activity (see discussion below).

The term "gene" includes structural genes and regions that have specific regulatory functions such as promoters and operators. The term "gene" includes the open reading frame of the gene as well as the upstream and downstream regulatory sequences. The upstream regulatory region is also referred as the promoter region of the gene. The downstream regulatory region is also referred as the terminator sequence region. The inactivation of ldh and alsS may be accomplished by deletion of nucleotide sequences in chromosomal DNA which: (1) are involved in transcriptional regulation of the promoter, operator, or the like of the ldh, pflA, pflB, alsD and/or alsS gene; (2) a frameshift introduced such that lactate dehydrogenase, pyruvate formate lyase, pyruvate formate lyase activating enzyme, alpha-acetolactate decarboxylase and/or acetolactate synthase is/are not expressed as an active protein; or (3) the entire structural gene, or a portion thereof, encoding lactate dehydrogenase, pyruvate formate lyase, pyruvate formate lyase activating enzyme, alpha-acetolactate decarboxylase and/or acetolactate synthase has been deleted. In certain preferred embodiments, microorganisms in which the entire gene encoding lactate dehydrogenase, pyruvate formate lyase, pyruvate formate lyase activating enzyme, alpha-acetolactate decarboxylase and/or acetolactate synthase has been deleted are provided. Exemplary sequences for the lactate dehydrogenase gene and acetolactate synthase gene, alpha-acetolactate decarboxylase gene are provided in SEQ ID NOs: 1 and 2, respectively. The coding sequence of pyruvate formatelyase and pyruvate formate lyase activating enzyme are provided in SEQ ID NO: 3.

The phrase "portion of a structural gene" or the entire structural gene, or "a portion thereof," may refer to a single nucleotide deletion in the structural gene portion. The deletion is preferably a deletion of five to ten nucleotides in the structural gene, more preferably ten to 50 nucleotides, and yet more preferably 50 to 100 nucleotides. In some aspects of the invention, the entire structural gene may be deleted. Other aspects of the invention provide for the deletion of lactate dehydrogenase (ldh), pyruvate formate lyase (pflB), pyruvate formate lyase activating enzyme (pflA), alpha-acetolactate decarboxylase (alsD) and/or acetolactate synthase (alsS). The open reading frames of the genes encoding the aforementioned enzymes are indicated in the sequence listing. As discussed below, ldh and any combination of pflA, pflB, alsS and alsD can be deleted.

In one aspect, the mutation of the genes in the chromosome of the microorganism is accomplished without introducing genes or portions thereof from exogenous sources. Another aspect provides for the mutation of endogenous genes by the introduction of one or more point mutation(s) or by introducing one or more stop codon in the open reading frame of the endogenous gene that is being modified. In another aspect, the open reading frame of the endogenous gene can be deleted from the chromosomal DNA.

In certain aspects, an exogenous nucleotide sequence may be introduced to inactivate a target gene for the purpose of selecting a bacterial strain with a mutated gene having a desired phenotype. The exogenous nucleotide sequence introduced into the microbial genome can be subsequently removed in a seamless fashion without leaving behind any residual exogenous nucleotide sequence.

In one embodiment, biocatalysts are selected for their ability to produce D(−)-lactic acid at high titer, yield and volumetric productivity. One embodiment provides a biocatalyst capable of producing at least 0.5 mole of D(−)-lactic acid for every one mole of carbon source (e.g., glucose) consumed. Such biocatalysts may, optionally, have been selected using growth-based selection.

The term "titer" means the molar concentration of a particular compound in the fermentation broth. Thus in the fermentation process for the production of D(−)-lactic acid, a titer of 100 mM would mean that the fermentation broth at the time of measurement contained 100 mMoles of lactic acid per liter of the fermentation broth.

The term "yield" refers to the moles of particular compound produced per mole of the feedstock consumed during the fermentation process. Thus in the fermentative process for the production of D(−)-lactic acid using glucose as the feedstock, the term yield refers to the number of moles of D(−)-lactic acid produced per mole of glucose consumed.

The term "volumetric productivity" refers to the amount of particular compound in grams produced per unit volume per unit time. Thus a volumetric productivity value of 0.9 g L$^{-1}$ h$^{-1}$ for D(−)-lactic acid would mean that 0.9 gram of D(−)-lactic acid is accumulated in one liter of fermentation broth during an hour of growth. The volumetric productivity range of the genetically modified organisms disclosed herein can be up to 4 g L$^{-1}$ h$^{-1}$ for example, QZ19 can reach a volumetric productivity higher than 3 g L$^{-1}$ h$^{-1}$.

The terms "titer," "yield," and "volumetric productivity" as used in this disclosure also include "normalized titer," "normalized yield," and "normalized volumetric productivity." In the determination of the normalized titer, normalized yield, and normalized volumetric productivity, the volume of the neutralizing reagents added to the fermentation vessel in order to maintain the pH of the growth medium is also taken into consideration.

The term "(w/v)" refers to the amount of a substance (in grams) per liter (g/L).

The terms "genetically engineered" or "genetically modified" as used herein refers to the practice of altering the expression of one or more enzymes in a microorganism by manipulating its genomic DNA. The terms "genetically modified microorganism(s)", "genetically modified bacterial strain(s) (GMBS)" and "biocatalyst(s)" may be used interchangeably within this disclosure. In certain embodiments, various *Bacillus* spp., e.g., *Bacillus coagulans* strains, *Bacillus licheniformis* strains, *Bacillus subtilis* strains, *Bacillus amyloliquifaciens* strains, *Bacillus megaterium* strains, *Bacillus macerans* strains, *Paenibacillus* spp. strains or *Geobacillus* spp, such as *Geobacillus stearothermophilus* strains can be genetically modified. Other *Bacillus* strain can be obtained from culture collections such as ATCC (American Type Culture Collection) and genetically engineered as set forth herein for the production of D(−)-lactic acid. In some embodiments of the invention, the *B. coagulans* strain Suy27-13 and/or *B. coagulans* strains containing the point mutation found in Suy27-13 may be specifically excluded from the scope of the claims.

Thus in one aspect, a process for the production of lactic acid in commercially significant quantities from the carbon compounds by genetically modified bacterial strains is provided. Microorganisms suitable for the production of D(−)-lactic acid can be cultured in one or two-step processes as disclosed herein. For any of the method steps, the genetically modified microorganisms may be maintained at a temperature between about 30° C. and about 65° C. Various embodiments contemplate culturing the microorganisms at a temperature of about 30° C., 37° C. or 55° C. Other embodiments contemplate culturing the microorganisms at a temperature between about 37° C. and about 65° C., between about 37° C. and about 55° C., between about 45° C. and about 60° C. or between about 45° C. and about 50° C.

"Mutation" or "inactivation" refers to genetic modifications done to the gene including the open reading frame, upstream regulatory region and downstream regulatory region. The gene mutations result in a down regulation or complete inhibition of the transcription of the open reading frame (ORF) of the gene. Gene mutations can be achieved either by deleting the entire coding region of the gene (ORF) or a portion of the coding nucleotide sequence (ORF), by introducing a frame shift mutation within the coding region, by introducing a missense mutation, insertion of sequences that disrupt the activity of the protein encoded by the gene, by introducing a stop codon or any combination of the aforementioned gene mutations.

As used herein, the term "exogenous" is intended to mean that a molecule or an activity derived from outside of a cell is introduced into the host microbial organism. In the case of an exogenous nucleic acid molecule introduced into the microbial cell, the introduced nucleic acid may exist as an independent plasmid or may get integrated into the host chromosomal DNA. In certain embodiments, exogenous nucleic acid encoding a protein is not found in the biocatalysts disclosed herein. Other embodiments allow for biocatalysts containing exogenous genes. Where present, an exogenous gene (nucleic acid sequence) may be introduced into the microbial cell in an expressible form with its own regulatory sequences such as promoter and terminator sequences. Alternatively, the exogenous nucleic acid molecule may get integrated into the host chromosomal DNA and may be under the control of the host regulatory sequences.

The term "endogenous" refers to the molecules and activity that are naturally (natively) present within the host cell. When used in reference to a biosynthetic activity, the term "exogenous" refers to an activity that is introduced into the host reference organism. The source can be, for example, a homologous or heterologous encoding nucleic acid that expresses the referenced activity following introduction into the host microbial organism. If the nucleic acid coding for a protein is obtained from the same species of the microbial organism, it is referred as homologous DNA. If the nucleic acid is derived from a different microbial species, it is referred as heterologous DNA. Irrespective of the nature of the DNA, whether it is homologous or heterologous, when introduced into a host cell, the DNA as well as the activity derived from that introduced DNA is referred to as exogenous. Therefore, exogenous expression of an encoding nucleic acid can utilize either or both heterologous and homologous encoding nucleic acid.

One aspect provides GMBS showing impressive titers, high yield and significant volumetric productivity for D(−)-lactic acid. The microorganisms disclosed herein can be employed in a production process for producing D(−)-lactic acid using various sugars. In one embodiment, the genetic modifications involve only the manipulation of genes within the native genome of the microorganism. In that embodiment, no exogenous genetic material such as plasmids bearing antibiotic resistance genes or any other exogenous nucleotide sequences coding for certain enzyme proteins is present in the bacterial strain for D(−)-lactic acid production.

Figure 7:
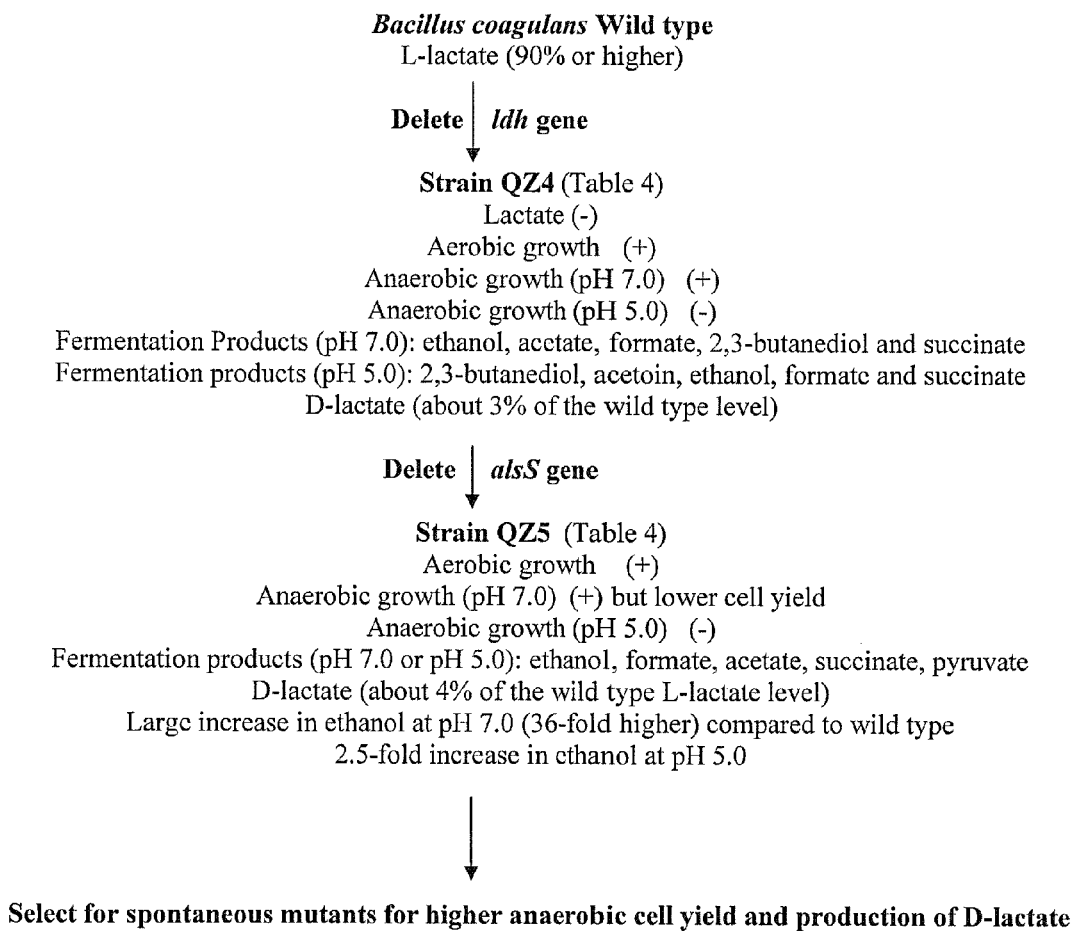
FIG. 7. Exemplary schematic for production of D(−)-lactic acid producing bacterial strains. Generally, the target bacterial strain/cell will be genetically modified to inactivate the activity of L-lactate dehydrogenase and acetolactate synthase, competing reactions at the pyruvate node. Cells will then be cultured under O$_2$-limiting conditions at a pH of between 4.5 and 5.5. Cells producing higher cell yields and/or production of lactic acid as compared to the parent strain are selected for further development. Selected cells are then cultured under O$_2$-limiting/anaerobic conditions at a pH between about 6.5 and 7.5. Cells producing higher cell yields and/or production of lactic acid as compared to the original selected strain are selected for further development or use in the production of D(−)-lactic acid. In certain preferred aspects of the invention, the cells used for the production of D(−)-lactic acid produce at least 60 g of lactic acid per liter of culture medium (preferably within about 48 hours).

The present invention combines the technique of specific genetic modifications with a process of growth-based selection to obtain strains showing high yield, titer and volumetric productivity for D(−)-lactic acid production. The genetically modified microbial strains produced by the disclosed methods may be subsequently grown in under various conditions, such as low pH, for several generations to select a clone producing D(−)-lactic acid at levels higher than the original parental strain and/or which has a higher cell yield as compared to parental strain. An exemplary scheme in this regard is shown in FIG. 7. This process for the growth-based selection of a clone with the most preferred phenotype is referred as growth-based selection.

During growth-based selection, the genetically modified strain is repeatedly transferred into fresh medium for a period of time to obtain a clone that exhibits fast/higher cell growth, rapid consumption of different carbon sources, ability to use multiple sugars simultaneously, ability to tolerate toxic chemicals in the carbon source and high production yield and productivity of the desired organic acid coupled with the low production of other organic acids. During growth-based selection, attention is paid to select the clone with the desirable phenotypes discussed above. A clone resulting from the selection process showing a very good growth rate but that has not improved in the yield of the desired organic acid is not a desirable clone. In the practice of the disclosed methods, strains are selected by starting the culture of a genetically modified strain aerobically and conducting serial passaging of the strain under conditions that limit oxygen within the culture system (e.g., fermenter). Genetically modified microorganisms capable of growing under oxygen limiting conditions are selected for continued passaging until microaerobic or anaerobic conditions are reached. Microorganisms are then anaerobically cultured under increasing pH conditions and selected on the basis of D(−)-lactate production under the culture conditions. For any of the method steps, the genetically modified microorganisms may be maintained at a temperature between about 30° C. and about 65° C. Various embodiments contemplate culturing the microorganisms at a temperature of about 30° C., 37° C. or 55° C. Other embodiments contemplate culturing the microorganisms at a temperature between about 37° C. and about 65° C., between about 37° C. and about 55° C., between about 45° C. and about 60° C. or between about 45° C. and about 50° C.

Genetic manipulations can be done in several different stages accompanied by growth-based selection in between the stages of genetic manipulations. The genomic manipulations involve either altering the endogenous DNA sequences or completely removing specific DNA sequences from the genomic DNA. The genetic manipulations may also involve inserting a foreign DNA sequence within the genomic DNA sequence of the microorganism. Certain embodiments, the genetic manipulations are accomplished by means of removing specific DNA sequences from the genomic DNA of the microorganisms without introducing any foreign DNA. Certain genetic manipulations necessary to inactivate the expression of a gene coding for a particular protein product requires an insertion of a foreign DNA sequence into the genome of the microorganism to select a clone with the desired genetic modification. For example, exogenous antibiotic marker genes can be used to insertionally inactivate the endogenous genes and to select the clone with the desired genotype. In one embodiment of the present invention, the introduced exogenous DNA sequences are ultimately removed from the genomic DNA of the microorganism so that the microorganism at the end of the genetic engineering process would have little or no exogenous DNA in its resulting genomic DNA, particularly no exogenous DNA genes (or portions thereof). Various genetic engineering techniques necessary for accomplishing the objectives of the preferred embodiment of the present invention are known in the art, including the use of plasmids exhibiting instability at elevated temperatures (see, for example, the material and methods discussed in the Examples of this application). Any cited scientific publications as well as patent documents are incorporated by reference in their entirety for the purpose of providing any necessary details for genetic engineering techniques useful for the present invention.

In one embodiment of the present invention, one or more of the genes coding for the proteins known to function in fermentative pathways are inactivated through one or more genetic manipulations or genetic engineering techniques as discussed above. Genes and enzymes that may be inactivated include: ldh, lactate dehydrogenase; and alsS, acetolactate synthase.

Accordingly, the following non-limiting embodiments are provided:

1. A bacterial cell comprising genetic modifications causing the inactivation of enzymatic activity for:

a) lactate dehydrogenase and optionally acetolactate synthase and/or pyruvate formate lyase;
b) lactate dehydrogenase and acetolactate synthase;
c) lactate dehydrogenase, acetolactate synthase and pyruvate formate lyase or
d) any of the following combinations of enzymatic activity: lactate dehydrogenase+pyruvate formate lyase; lactate dehydrogenase+pyruvate formate lyase activating enzyme; lactate dehydrogenase+pyruvate formate lyase activating enzyme+pyruvate formate lyase; lactate dehydrogenase+acetolactate synthase; lactate dehydrogenase+alpha-acetolactate decarboxylase; lactate dehydrogenase+acetolactate synthase+alpha-acetolactate decarboxylase; lactate dehydrogenase+pyruvate formate lyase+acetolactate synthase; lactate dehydrogenase+pyruvate formate lyase+alpha-acetolactate decarboxylase; lactate dehydrogenase+pyruvate formate lyase activating enzyme+acetolactate synthase; lactate dehydrogenase+pyruvate formate lyase activating enzyme+alpha-acetolactate decarboxylase; lactate dehydrogenase+pyruvate formate lyase activating enzyme+pyruvate formate lyase+acetolactate synthase; lactate dehydrogenase+pyruvate formate lyase activating enzyme+pyruvate formate lyase+alpha-acetolactate decarboxylase; lactate dehydrogenase+pyruvate formate lyase activating enzyme+alpha-acetolactate decarboxylase+acetolactate synthase; lactate dehydrogenase+pyruvate formate lyase+alpha-acetolactate decarboxylase+acetolactate synthase; lactate dehydrogenase+pyruvate formate lyase activating enzyme+pyruvate formate lyase+alpha-acetolactate decarboxylase+acetolactate synthase.

2. The bacterial cell according to embodiment 1, further comprising genetic modifications causing the inactivation of a desired enzymatic activity.

3. The bacterial cell according to embodiment 1 or 2, further comprising genetic modifications introducing exogenous genes into said bacterial cell.

4. The bacterial cell according to embodiment 1 or 2, wherein said genetic modification comprises the mutation of a gene encoding lactate dehydrogenase (ldh), pyruvate formate lyase (pflB), pyruvate formate lyase activating enzyme (pflA), alpha-acetolactate decarboxylase (alsD) and/or acetolactate synthase (alsS) or the deletion of all or a portion of a gene encoding lactate dehydrogenase (ldh), pyruvate formate lyase (pflB), pyruvate formate lyase activating enzyme (pflA), alpha-acetolactate decarboxylase (alsD) and/or acetolactate synthase (alsS).

5. The bacterial cell according to embodiment 4, the mutation of said genes comprises the introduction of one or more point mutation(s) or the introduction of one or more stop codon in the open reading frame of the gene.

6. The bacterial cell according to embodiment 1-3, wherein said genetic modification comprises a point mutation or a deletion in the coding sequence/open reading frame(s) of lactate dehydrogenase (ldh), pyruvate formate lyase (pflB), pyruvate formate lyase activating enzyme (pflA), alpha-acetolactate decarboxylase (alsD) and/or acetolactate synthase (alsS) or insertion of an exogenous sequence into the coding region/open reading frame(s) of lactate dehydrogenase (ldh), pyruvate formate lyase (pflB), pyruvate formate lyase activating enzyme (pflA), alpha-acetolactate decarboxylase (alsD) and/or acetolactate synthase (alsS).

7. The bacterial cell according to any one of embodiments 1, 2, 4, 5 or 6, wherein said bacterial cell does not contain exogenous genes or portions thereof.

8. The bacterial cell according to any one of embodiments 1, 2, 4, 5 or 6, wherein enzymatic activity of L-lactate dehydrogenase, pyruvate formate lyase and/or acetolactate synthase is inactivated by homologous recombination, optionally using a plasmid sensitive to temperature.

9. The bacterial cell according to embodiment 8, wherein said genetic modification comprises complete or partial deletion of nucleotides encoding acetolactate synthase, lactate dehydrogenase and/or pyruvate formate lyase.

10. The bacterial cell according to any one of embodiments 1-9, wherein:
a) said bacterium is a *Bacillus* spp., such as *Bacillus coagulans, Bacillus licheniformis, Bacillus subtilis, Bacillus amyloliquifaciens, Bacillus pumilus, Bacillus circulans* or *Bacillus thiaminolyticus*; and
b) wherein *Bacillus coagulans* Suy27-13 may be optionally excluded from the scope of the claims.

11. A genetically modified bacterial cell according to any one of embodiments 1-10, wherein said genetically modified bacterial cell is QZ15 or QZ19.

12. A method of producing D(−)-lactic acid comprising culturing a genetically modified bacterial cell according to any one of embodiments 1-11 in a medium comprising a carbon source under conditions that allow for the production of D(−)-lactic acid.

13. The method according to embodiment 12, further comprising isolating or purifying the D(−)-lactic acid.

14. The method according to embodiment 13, wherein said bacterial strain is cultured under anaerobic conditions.

15. The method according to embodiments 12-14, wherein said medium comprises between 2% and 20% (w/v) carbon source.

16. A method of making a D(−)-lactic acid producing genetically modified bacterial cell comprising:
a) inactivation of lactate dehydrogenase and acetolactate synthase activity in said bacterial cell;
b) culturing said bacterial cell at a pH between 3.0 and 6.0 under aerobic and/or oxygen-limiting conditions in a medium containing a carbon source;
c) selecting a bacterial cell exhibiting increased cell yield and/or D(−)-lactic acid production as compared to the parental strain;
d) culturing the selected bacterial cell at a pH of between 6.5 and 8.0 under anaerobic conditions in a medium containing a carbon source; and
e) selecting a bacterial cell exhibiting increased cell yield and/or D(−)-lactic acid production as compared to the parental bacterial cell or the bacterial cell selected in step d).

17. The method according to embodiment 16, wherein step b) is performed at a pH of:
a) about 4.5 or 5.5; or
b) about 5.0.

18. The method according to embodiment 16, wherein step d) is performed at a pH of:
a) about 6.5 to about 7.5; or
b) about 7.0.

19. The method according to embodiments 16-18, wherein steps d) and e) are repeated in medium containing increasing amounts of a carbon source.

20. The method according to embodiments 16-18, wherein steps b) and c) are repeated in medium containing increasing amounts of a carbon source.

21. The method according to embodiments 16-18, wherein steps b)-e) are repeated in medium containing increasing amounts of a carbon source.

22. The method according to embodiments 12-21, wherein the carbon source is glucose, fructose, xylose, arabinose, galactose, mannose, rhamnose, sucrose, cellobiose, hemicelluloses, cellulose, glycerol or combination thereof.

23. The method according to embodiments 12-15, wherein said fermentation is conducted under anaerobic conditions at a pH of:
a) about 6.5 to about 7.5; or
b) about 7.0.

24. The method according to embodiments 12-22, wherein said genetically modified bacterial cell produces at least 60 g of lactic acid per liter, at least 80 g of lactic acid per liter, or at least 90 g of lactic acid per liter of fermentation medium within 48 hours of the start of fermentation.

25. The method according to embodiments 12-24, wherein the pH of medium used to culture said genetically modified bacterial cell is maintained by the automatic addition of acid or base.

26. The method according to embodiments 16-23, wherein said genetically modified bacterial cell is initially cultured under aerobic conditions and serially passaged under conditions that reduce the amount of oxygen present in the culture system until microaerobic or anaerobic conditions are reached.

27. The method according to embodiments 16-23 or 26, wherein the bacterial cell a *Bacillus* spp., such as *Bacillus coagulans, Bacillus licheniformis, Bacillus subtilis, Bacillus amyloliquifaciens, Bacillus pumilus, Bacillus circulans* or *Bacillus thiaminolyticus*; wherein *Bacillus coagulans* Suy27-13 may be optionally excluded.

28. The bacterial cell or method of any one of embodiments 1-10 and 12-27, wherein the bacterial cell has one of the following combinations of gene inactivations: ldh+pflB; ldh+pflA; ldh+pflA+pflB; ldh+alsS; ldh+alsD; ldh+alsS+alsD; ldh+pflB+alsS; ldh+pflB+alsD; ldh+pflA+alsS; ldh+pflA+alsD; ldh+pflA+pflB+alsS; ldh+pflA+pflB+alsD; ldh+pflA+alsD+alsS; ldh+pflB+alsD+alsS; ldh+pflA+pflB+alsD+alsS; or inactivation of one of the following combinations of enzymatic activity: lactate dehydrogenase+pyruvate formate lyase; lactate dehydrogenase+pyruvate formate lyase activating enzyme; lactate dehydrogenase+pyruvate formate lyase activating enzyme+pyruvate formate lyase; lactate dehydrogenase+acetolactate synthase; lactate dehydrogenase+alpha-acetolactate decarboxylase; lactate dehydrogenase+acetolactate synthase+alpha-acetolactate decarboxylase; lactate dehydrogenase+pyruvate formate lyase+acetolactate synthase; lactate dehydrogenase+pyruvate formate lyase+alpha-acetolactate decarboxylase; lactate dehydrogenase+pyruvate formate lyase activating enzyme+acetolactate synthase; lactate dehydrogenase+pyruvate formate lyase activating enzyme+alpha-acetolactate decarboxylase; lactate dehydrogenase+pyruvate formate lyase activating enzyme+pyruvate formate lyase+acetolactate synthase; lactate dehydrogenase+pyruvate formate lyase activating enzyme+pyruvate formate lyase+alpha-acetolactate decarboxylase; lactate dehydrogenase+pyruvate formate lyase activating enzyme+alpha-acetolactate decarboxylase+acetolactate synthase; lactate dehydrogenase+pyruvate formate lyase+alpha-acetolactate decarboxylase+acetolactate synthase; lactate dehydrogenase+pyruvate formate lyase activating enzyme+pyruvate formate lyase+alpha-acetolactate decarboxylase+acetolactate synthase.

29. The bacterial cell according to any of embodiments 1-11 or 28, wherein the bacterial cell produces D(−)-lactic acid at a temperature between about 30° C. and 65° C.; between about 37° C. and about 65° C.; between about 37° C. and about 55° C.; between about 45° C. and about 60° C.; between about 45° C. and about 50° C.; or at a temperature of about 30° C.; about 37° C.; or about 55° C.

30. The method according to any of embodiments 12-28, wherein the method comprises culturing the bacterial cell at a temperature between about 30° C. and about 65° C.; between about 37° C. and about 65° C.; between about 37° C. and about 55° C.; between about 45° C. and about 60° C.; between about 45° C. and about 50° C.; or at a temperature of about 30° C.; about 37° C.; or about 55° C.

Microorganisms were deposited with the Agricultural Research Service Culture Collection, 1815 N. University Street, Peoria, Ill., 61604 U.S.A (Table 5). These cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The following examples are provided as way of illustrating the present invention. These inventions in no way limit the scope of this invention. A person experienced in the field of industrial microbiology would be able to practice the present invention in several different embodiments without violating the spirit of the present invention.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Construction of a D(−)-Lactic Acid Producing Thermotolerant *Bacillus coagulans*

Materials and Methods
Bacterial Strains and Plasmids

*B. coagulans* wild type strain P4-102B was described previously (27). *Escherichia coli* strain Top10 (Invitrogen) and *Bacillus subtilis* strain HB1000 (11) were used as hosts during construction of various plasmids used in this study. Plasmid pGK12 carries chloramphenicol and erythromycin resistance genes and replicates in several Gram-positive bacteria and *E. coli* (17, 21). Although this plasmid has a broad host-range, its replication is naturally restricted to temperatures ≤42° C. This temperature sensitive nature of plasmid pGK12 replication at 50° C. provides an opportunity to select for chromosomal DNA integrants of *B. coagulans* that can grow at 50-55° C. Plasmid pGK12 and its derivatives were maintained in *B. subtilis* strain HB1000 at 37° C. When transformed into *B. coagulans*, the transformants were selected and maintained at 37° C. *B. coagulans* mutant strains and plasmids used in the construction of mutants are listed in Table 1.

Medium and Growth Condition

L-broth (LB) (19) was used as the rich medium for culture of bacteria at pH 5.0 or 7.0, as needed. Glucose was sterilized separately and added to the medium at the indicated concentration, before inoculation. Chloramphenicol, erythromycin and ampicillin were added to LB medium at 7.5 mg/L, 5 mg/L and 100 mg/L, respectively, when needed. Calcium carbonate medium was prepared by overlaying glucose-supplemented (2%, w/v) LB-agar medium with 2.5 ml of $CaCO_3$ agar (solid $CaCO_3$ suspended in water (1% w/v) with 1.5% agar) as described previously (30).

Aerobic cultures were grown in a shaker at 200 RPM. Fermentations were carried out either in small custom fermenters (2) or 2.5 L fermenters (New Brunswick Scientific Bioflo 110). Culture pH was maintained at the set value by automatic addition of 2N or 6N KOH. Solid $CaCO_3$ (Fisher Scientific, Pittsburgh, Pa.) was added at the beginning of fermentation, as needed, at a concentration of 2.0% (w/v) unless specified otherwise. Inoculum for these cultures was grown in the same medium aerobically at 50° C. overnight and fermentations were started with 1% (v/v) inoculum. Samples were removed periodically for determination of fermentation products and residual sugar concentration.

Construction of Deletion Mutants of *B. coagulans*

Isolation of deletion mutants of *B. coagulans* was based on previously described methods in which a plasmid DNA containing the two ends of the target gene was integrated into the chromosome at the target site with appropriate DNA sequence homology using a single recombination event. Such recombinants with appropriate antibiotic resistance can be easily identified using replication-conditional plasmids at the restrictive temperature that eliminates the intact plasmid from the cytoplasm (13). The plasmid DNA and associated antibiotic resistance gene are subsequently removed from the chromosome by a single homologous recombination of different parts of the introduced plasmid DNA and appropriate chromosomal DNA leaving a deletion of the target gene. In the construction of an ldh gene deletion of *B. coagulans*, plasmid vectors that can not replicate in *B. coagulans* were initially employed. However, using such plasmids, chromosomal insertions of the introduced plasmid DNA was not detected. This could be a consequence of plasmid transformation efficiency of *B. coagulans* strain P4-102B being lower (29) than the potential recombination frequency of the incoming plasmid to the chromosome. To overcome these low frequency events, plasmid pGK12 was used as the primary vehicle for transfer of DNA to *B. coagulans* for deletion construction. Plasmid pGK12 is stable in *B. coagulans* at 37° C. and not 50° C. Presence of plasmid in each cell in a population ($10^9$ CFU/ml) at 37° C. helps to overcome the low transformation efficiency of plasmid DNA into this bacterium. The large population of cells with the plasmid DNA allows selection of rare recombination events between the homologous regions of the plasmid DNA and chromosome. These rare recombinants in the population of cells that have the plasmid DNA (along with the antibiotic resistance gene) integrated into the chromosome can be readily identified when the plasmid DNA is eliminated from the cells after growth at 50-55° C.

Isolation of Δldh Mutant Strain

For construction of ldh deletion derivative, two sets of primers were used [primers 9 (BsaAI), 10 (EcoRI) and 11 (EcoRI), 12 (StuI)] (Table 2) to amplify the 5' and 3'-ends of the ldh gene separately using the genomic DNA from *B. coagulans* strain P4-102B as template. These primers have unique endonuclease recognition sequences at the 5'-end. The two amplified fragments were digested with EcoRI and ligated together. The ligation product was used as template (primers 9 and 12) to produce a promoterless ldh gene fragment that is lacking a 100 bp region in the middle of the ldh starting at 431 bp from the "A" in the "ATG" of the ldh gene. This fragment was digested with BsaAI and StuI and then ligated to similarly digested plasmid pGK12 (plasmid pQZ44). Insert in this plasmid was confirmed by sequencing. Plasmid pQZ44 was transformed into strain P4-102B and erythromycin resistant colonies were selected at 37° C. One of the transformants was cultured at 50° C. and an erythromycin-resistant derivative that was also L-LDH-minus (about 1%) was selected (strain QZ3). Presence of the plasmid DNA in the ldh gene in the chromosome of strain QZ3 was confirmed by PCR amplification of the genomic DNA with appropriate primers and sequencing the amplified product. During sub-cultures in medium without erythromycin, the ldh-minus property of strain QZ3 was found to be unstable and ldh$^+$ revertants were readily isolated. Strain QZ3 was serially transferred into fresh medium (1% v/v inoculum) everyday at 55° C. without erythromycin for 10 days. The final culture was diluted and plated on LB-agar medium. After overnight growth at 50° C., the colonies were transferred by replica plating to LB-agar, LB-agar+erythromycin and calcium carbonate medium (LB-agar supplemented with glucose and $CaCO_3$ (30)). The colonies that grew on LB-agar, but not on LB-agar+erythromycin and also did not produce lactate based on the extent of clearing in calcium carbonate medium were picked and tested further in liquid cultures for lactate production. The second recombination is expected to yield erythromycin sensitive derivatives lacking L-LDH activity because of the 100 bp deletion in the ldh gene. In these experiments the frequency of Δldh was 1 of 5000 erythromycin-sensitive colonies. One of these Δldh mutants, strain QZ4 was selected for further study.

Using similar methods, a Δldh mutant could not be isolated using chloramphenicol resistance as a selective marker. Irrespective of the plasmid backbone, presence of chloramphenicol resistance gene was found to target plasmid DNA insertion to a unique location in the chromosome that is unrelated to the *B. coagulans* chromosomal DNA in the plasmid (Su and Rhee, unpublished data). These results indicate that chloramphenicol resistance gene is unsuitable for mutant construction in this *B. coagulans* strain.

Construction of a Δals Mutant

A mutant derivative of strain QZ4 lacking acetolactate synthase activity is not expected to produce acetoin and 2,3-butanediol, fermentation products produced by ldh mutant of *B. coagulans* (30). As a first step towards the construction of this double mutant (Δldh Δals), the alsD (alpha-acetolactate decarboxylase) and alsS (acetolactate synthase) sequences were amplified by PCR from the genomic DNA of strain P4-102B using primers 17 and 21. This PCR fragment was treated with T4 polynucleotide kinase and ligated to HincII digested plasmid vector pUC19 to form plasmid pQZ45. This alsSD DNA insert in plasmid pQZ45 was verified by sequencing with appropriate primers. Primers 18 and 22 were used to amplify by PCR a 2,380 bp DNA from plasmid pQZ45 containing only the alsSD coding regions (without the promoter). The amplified DNA was cloned into the HincII site of plasmid pUC19 generating plasmid pQZ45-1. A 596 bp region of the alsS was removed from plasmid pQZ45-1 after digestion by AfeI and HincII and an erythromycin-resistance gene cassette was inserted at that location. This new plasmid, pQZ54 served as template (primers 18 and 22) to amplify a fragment with the alsSD genes with a 596 bp deletion in alsS and the gene encoding erythromycin resistance. The PCR product was phosphorylated with polynucleotide kinase and ligated to plasmid pGK12 digested with BsaAI and AfeI. The resulting plasmid, pQZ64 was transformed into *B. coagulans* strain QZ4 (Δldh) by electroporation and erythromycin-resistant colonies were selected at 37° C. Using the procedures described above for construction of Δldh, a ΔalsS mutation was introduced into strain QZ4. This method yielded several alsS mutants differing in their growth rates under both aerobic and anaerobic condition. One of the mutants with the highest growth rate (strain QZ5) was selected for further study.

Transformation of *E. coli*, *B. Subtilis* and *B. Coagulans*

*E. coli* transformation was based on standard technique as described previously. *Bacillus subtilis* strain HB1000 was transformed according to the procedure described by Boylan et al. (4) with some changes. Cells from an overnight culture in stationary phase of growth in LB medium was inoculated (10% v/v) into 10 ml of freshly prepared modified competence medium (29), which contained 100 mM phosphate buffer (pH 7.0), 3 mM trisodium citrate, 3 mM magnesium sulfate, 2% glucose, 22 μg/ml ferric ammonium citrate, 0.1% casein hydrolysate and 0.2% potassium glutamate, in a 125 ml Erlenmeyer flask and incubated at 37° C. with shaking for 3 h. When the $OD_{600\ nm}$ reached around 0.6, 0.6 ml of the culture was removed to a 13×100 mm test tube and DNA was added to the cells. This culture with DNA was incubated in a rotator at 37° C. for 2.5 hours. Cells were collected by centrifugation at room temperature and resuspended in 0.1 ml of LB and plated on LB-agar with appropriate antibiotics. Plates were incubated at 37° C. and transformants were selected next day.

For transformation of wild type *B. coagulans* P4-102B, Cells growing in 10 ml of LB in a 125 ml flask at 50° C. ($OD_{420\ nm}$ 0.3) was inoculated (10% v/v) into 100 ml LB medium in a 1 liter flask. Cells were incubated at 50° C. with shaking (200 RPM) for about 3-4 h until the OD at 420 nm reached about 0.3-0.5. Cells were collected by centrifugation (4° C.; 4,300×g; 10 min) and washed three times with 30, 25 and 15 ml of ice-cold SG medium (sucrose, 0.5 M, glycerol, 10%). These electro-competent cells were used immediately. Seventy five μl of cell suspension was mixed with 0.1 μg of plasmid DNA and transferred to chilled electroporation cuvette (1 mm gap). The electroporation conditions (Bio-Rad electroporator) were set as square wave for 5 ms at 1.75 KV. After electroporation, cells were transferred to 2 ml of pre-warmed (37° C. or 50° C.) RG medium (LB medium with 0.5M sucrose, 55.6 mM glucose and 20 mM $MgCl_2$). These cells were transferred to a 13×100 mm screw cap tube and incubated in a tube rotator for 3 h at 50° C. before plating on selective antibiotic medium. For transformation of temperature sensitive plasmids, the regeneration temperature was 37° C. and the cultures were incubated overnight. For transformation of the mutant QZ4, the DNA concentration was increased to 1 μg plasmid DNA, and the electroporation condition was altered to a time constant of 10 ms at 1.5 KV, 25 μF and 600 ohms.

Growth-Based Selection for Spontaneous Mutants with Desired Phenotype

Since every microbial culture will have a certain number of spontaneous random mutations, a mutant with desired phenotype can be readily isolated from that population by providing a growth condition that would preferentially support growth of the specific mutant. Since Δldh ΔalsS mutant, strain QZ5, is anaerobic growth defective at a culture pH of 5.0, mutation(s) that would increase anaerobic growth by initiating a new fermentation pathway (for example, D-lactic acid production) is expected to have a growth advantage over the rest of the parent population. Achieving a higher anaerobic growth rate may require more than one mutation (to initiate the fermentation pathway, to enhance metabolic flux to that pathway by increasing enzyme concentration, etc.). Accumulation of beneficial mutations, each providing incremental increase in growth rate and/or product production, can be achieved by serial transfer of a culture until the desired number of mutations accumulates in a single cell and manifests as an identifiable phenotype. Since strain QZ5 is anaerobic growth defective, cultures were started in small pH controlled fermenters (250 ml in a 500 ml vessel) with air as the gas phase. As the culture starts to grow, severe $O_2$-limitation would limit growth and cell yield. Further increase in cell density would depend on the ability of the cell to ferment sugars present in the medium. To isolate a mutant derivative of strain QZ5 that can grow anaerobically, the fermenter culture was sequentially subcultured under indicated conditions using small pH controlled fermenters. The transfer conditions were adjusted to different time and inoculum amount. On an average, transfers were after every 2 or 3 days of growth with 2% inoculum during adaptation to increasing sugar concentration.

Determination of mRNA Levels

For determination of mRNA levels in *B. coagulans*, cells grown under different conditions were collected by centrifugation (16,000×g; 30 sec, room temperature). RNA was isolated using the acid phenol extraction method as described before (30). Total RNA concentration was determined from the absorbance at 260 nm (NanoVue, GE). The cDNA copy was prepared with Superscript III reverse transcriptase (Invitrogen) using primers specific for the gene of choice. The cDNA (mRNA) concentration was determined by PCR using gene specific primers and SYBR-green containing PCR reaction mix (Bio-Rad Laboratories, Hercules, Calif.). The threshold cycle for each of the PCR reaction with different concentrations of cDNA was determined and compared against a standard DNA template that was also run at the same time (16). From these results, a ratio of the concentration of gene-specific mRNA present in the sample was calculated. Reported results are the average of at least three experiments. The primers used for RT-PCR are listed in the Table 2; ldh primers—primer 23 and 24, pfl primers—primer 25 and 26, pdhA (E1α) primers—primer 27 and 28, d-ldh primers—primer 29 and 30, als primers—primer 31 and 32, polA primers used as internal control—primer 33 and 34.

Enzyme Analysis

To determine the level of PDH and LDH activity, cells were cultured in LB until the culture reached the mid- to late-exponential phase of growth. Cells were harvested by centrifugation (10,000×g, 10 min; room temperature), washed once with 10 ml of phosphate buffer (50 mM, pH 7.0) and resuspended in 5.0 ml of same phosphate buffer. Cells were broken by passage through a French pressure cell (20,000 PSI). All operations after this step were at 4° C. The cell extract was centrifuged at 12,000×g for 30 min to remove the cell debris and the supernatant was centrifuged again at 100,000×g (Beckman) for 1 h to remove large particulates and membrane vesicles. Supernatant was used for enzyme assay. PDH activity assay was based on pyruvate-dependent reduction of $NAD^+$ at 340 nm ($\varepsilon=6,220$ $M^{-1}$ $cm^{-1}$) as described previously (33). Each 1 ml reaction mixture contained potassium phosphate buffer (50 mM; pH 7.5), thiamine pyrophosphate (0.4 mM), CoA (0.13 mM), $MgCl_2.6H_2O$ (2 mM), dithiothreitol (2.6 mM), $NAD^+$ (0.75 mM) and crude extract. The reaction was started by the addition of pyruvate (5 mM). LDH activity was assayed as described previously (35) as the oxidation of NADH in the presence of pyruvate. Each 1 ml reaction mixture contained potassium phosphate buffer (50 mM; pH 7.5), NADH (0.1 mM) and crude extract. The reaction was started by the addition of pyruvate (25 mM). Protein concentration was determined by Bradford method with bovine serum albumin as standard (5).

Analytical Methods.

Glucose and fermentation products were determined by HPLC with the Aminex HPX-87H ion exclusion column (300 mm×7.8 mm) as described previously (32). Optical isomers of D-(−)- and L-(+)-lactic acids were determined by HPLC with a Chirex 3126(D)-penicillamine column (150×4.6 mm, 5 micron) (Phenomenex) with 2 mM $CuSO_4$ as eluent. The D-(−)-lactate was also analyzed by enzyme-based method with D-lactate dehydrogenase (Sigma Chemical Co., St, Louis, Mo.).

Materials

Biochemicals were from Sigma Chemical Co. (St. Louis, Mo.) and organic and inorganic chemicals were from Fisher Scientific (Pittsburgh, Pa.). Molecular biology reagents and supplies were from New England Biolabs (Ipswich, Mass.), Invitrogen or Bio-Rad Laboratories.

Results and Discussion

Sprorogenic lactic acid bacteria such as *B. coagulans* produce L(+)-lactic acid as the primary fermentation product irrespective of the carbon source (glucose, xylose, cellobiose, etc.) (10, 27, 28). In support of this, the mRNA encoding ldh gene was present at the highest level among the genes encoding proteins at the pyruvate node, irrespective of the growth pH or growth stage (Table 3) (30). A gene encoding D(−)-lactate dehydrogenase (ldhA) has been identified in *B. coagulans*, cloned and expressed in *Escherichia coli* in an active form. However, the level of D(−)-lactate in the fermentation broth of *B. coagulans* never exceeded 5% of the total lactic acid produced and most of the fermentation broths indeed lack detectable D(−)-lactic acid (27). The level of ldhA mRNA level in the cell was less than 0.5% of the ldh mRNA level (Table 3).

Small amounts of acetate, ethanol and formate are also produced by *B. coagulans* during sugar fermentation, especially during fermentation of pentoses, such as xylose indicating the presence of an active pyruvate formate-lyase (27). Although the genes encoding the enzymes in the 2,3-butanediol pathway are present in the sequenced genome of *B. coagulans*, 2,3-butanediol was not detected in the fermentation broth of wild type *B. coagulans* irrespective of the growth pH. This is apparently a consequence of poor expression of the alsSD operon in the wild type (Table 3) or the flux to lactate is high enough to deplete the pyruvate pool. In order to construct a derivative of *B. coagulans* that produces D(−)-lactic acid as the major fermentation product, the primary fermentation pathway to L(+)-lactic acid catalyzed by L-LDH (ldh) needs to be deleted and the level of expression of ldhA encoding D-LDH needs to be enhanced.

Construction of a Δldh Mutant

A *B. coagulans* mutant lacking L-LDH activity described previously (30) produced acetate, ethanol, formate and 2,3-butanediol as fermentation products but not D(−)-lactate. This ldh mutant, Suy27-13, carried a single base change in the ldh gene and was subject to reversion during anaerobic growth, especially during growth at pH 5.0. In order to overcome the high reversion rate of the ldh mutation in strain Suy27-13, the ldh gene was deleted.

Several methods for constructing gene deletions in bacteria are available and many of these utilize appropriate linear DNA with a positive selection gene such as an antibiotic resistance gene flanked by short DNA sequence corresponding to the target gene (7, 20, 24). However, attempts to construct Δldh mutants using linear DNA were unsuccessful in *B. coagulans*. This could be a result of low transformation efficiency of *B. coagulans* combined with the need for the incoming DNA to recombine to yield selectable transformants. In order to overcome this limitation, an alternate method that has proven useful in gene deletions was used (13). A temperature sensitive plasmid with appropriate target ldh gene sequence and erythromycin resistance gene was constructed (plasmid pQZ44). After transformation of *B. coagulans* strain P4-102B by electroporation, plasmid pQZ44-containing transformants were selected at 37° C. that supported stable maintenance of the plasmid. Continued culturing of this plasmid-containing derivative is expected to mobilize the plasmid to the chromosome in a fraction of the population by a single recombination at the ldh gene. During growth at 50° C., due to the inability of the plasmid to replicate at this temperature, plasmids will be cured off the cells and erythromycin-resistant colonies that appear at 50° C. are expected to have the plasmid DNA at the chromosomal ldh gene. Further cultivation of these derivatives will lead to DNA rearrangements leading to deletion of the target gene ldh. One such ldh mutant, strain QZ4, was identified by the loss of erythromycin resistance and absence of lactate as a fermentation product (Table 3 & 4). In agreement with the previous report on ldh mutant (30), anaerobic growth of strain QZ4 was very minimal even in rich medium with glucose at pH 5.0.

Properties of the Δldh Strain QZ4

Figure 1B:
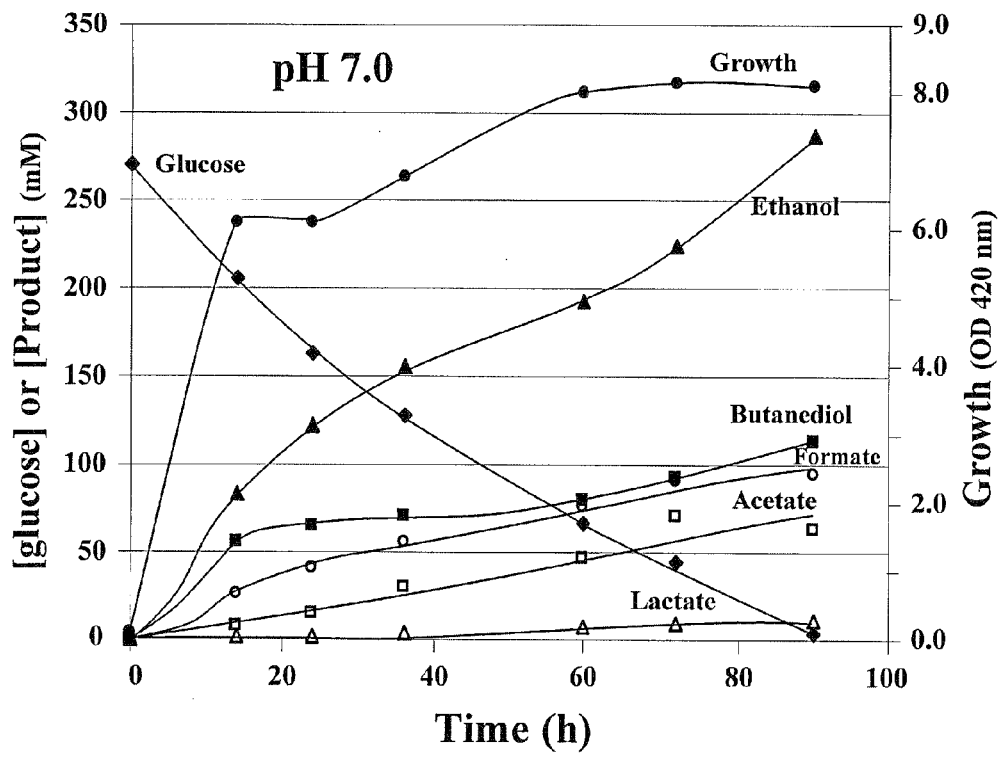

The ldh mutant strain QZ4 produced ethanol as the main fermentation product when cultured at pH 7.0 and 2,3-butanediol as the primary product during growth and fermentation at pH 5.0 (Table 4; FIG. 1). Both PFL and PDH contributed acetyl-CoA to ethanol production at pH 7.0 and the contribution of PDH to ethanol was calculated to be about 80% based on the amount of formate in the broth. In support of the PDH-based ethanol production, the PDH activity was about 2-fold higher in the mutant grown in pH 7.0 fermentations during the exponential phase of growth (Table 2). However, the PDH activity declined as the culture entered stationary phase in contrast to an increase in activity in the parent strain at the same growth stage. At pH 5.0, anaerobic growth of the mutant was undetectable and pH controlled fermentation started with air in the gas phase ($O_2$-limiting condition) did allow growth of the mutant. However, as the $O_2$ became very limiting due to increase in cell density, growth stopped and the final cell yield of the pH 5.0 fermentation culture was only about ½ of the parent culture. In such an oxygen-limited fermentation, the ldh mutant produced very low level of ethanol compared to the pH 7.0 fermentations. Most of the product of the pH 5.0 culture was 2,3-butanediol (Table 4; FIG. 1).

The comparatively low level of expression of pflB gene in pH 5.0 cultures and low level of formate in the $O_2$-limited fermentation (Tables 3, 4; FIG. 1) suggest that at pH 5.0, the ldh mutant is phenotypically LDH- and PFL-minus. It has been reported previously that an ldh, pfl double mutant of *E. coli* is anaerobic minus (15) and the same characteristics is also carried through to *B. coagulans*. Although the ldh mutant produced 2,3-butanediol as the major fermentation product at pH 5.0, it failed to grow anaerobically using this fermentation pathway. This is apparently due to redox imbalance since introduction of small amount of $O_2$ into the pH 5.0 fermentation did support production of higher level of 2,3-butanediol and associated growth. Since butanediol is a significant fermentation product of the ldh mutant even during growth at pH 7.0, a double mutant, strain QZ5, lacking both L-LDH and ALS was constructed.

*B. coagulans* Δldh ΔalsS Double Mutant

Figure 2A:
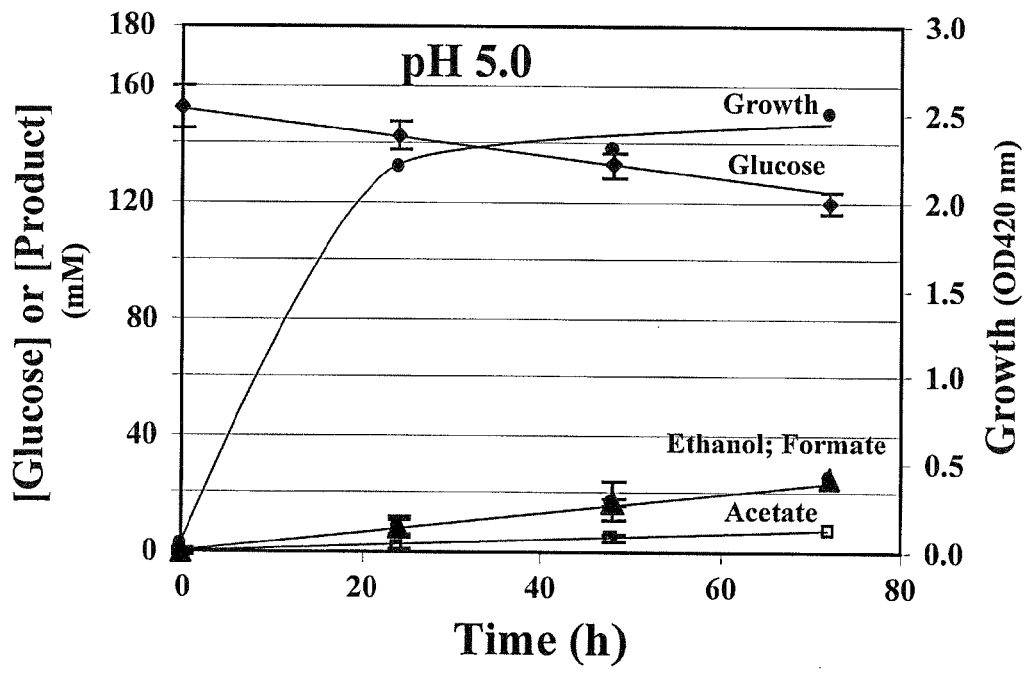
FIGS. 2A-B. Fermentation profile of *B. coagulans* strain QZ5 (Δldh, ΔalsS) at pH 5.0 (FIG. 2A) and pH 7.0 (FIG. 2B). Fermentations were in small fermenters with pH control by automatic addition of KOH in LB+glucose (30 g/L).
Figure 2B:
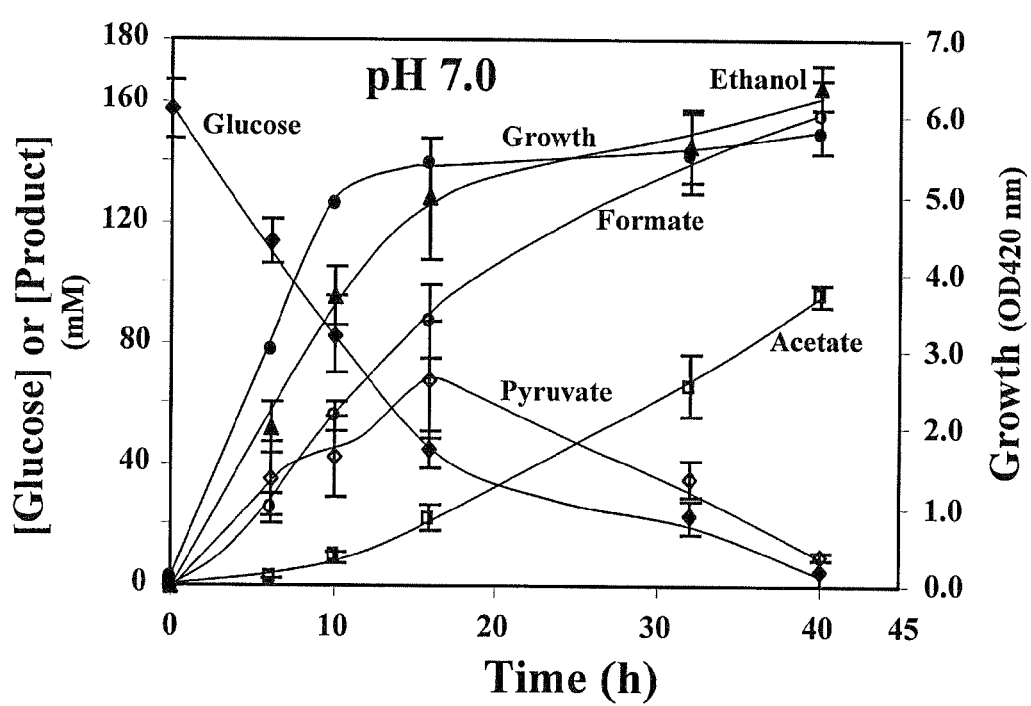

The ldh alsS double mutant, strain QZ5, grew aerobically at both pH 5.0 and 7.0. Anaerobic growth of the double mutant in pH-controlled fermentations that started aerobically was detectable only at pH 7.0, a property, the double mutant shared with the parent, strain QZ4 (FIG. 2). The primary products of the pH 7.0 fermentation were ethanol, formate, pyruvate and acetate. Significant amount of pyruvate in the fermentation broth of pH 7.0 cultures of the double mutant indicates that the PDH and PFL combined could not match the rate of glucose conversion to pyruvate by glycolysis. Neither the single or the double mutant produced L(+)-lactic acid at detectable level.

Since the double mutant produced significant amount of formate and other products of PFL activity, a triple mutant lacking the PFL activity was constructed. However, this triple mutant lacking L-LDH, ALS and PFL activities failed to grow anaerobically under all conditions tested and was not used further.

Growth-Based Selection for D(−)-Lactic Acid Production

The small amount of lactic acid produced by the double mutant was D(−)-lactic acid (Table 4). Increasing the level of D(−)-lactic acid production is expected to support anaerobic growth of the double mutant as the case with the wild type strain that can grow anaerobically with L(+)-lactic acid as the primary fermentation product. The ldh mutant strain did produce higher level of ldhA mRNA compared to the wild type irrespective of the culture pH (Table 3). Very low level of PFL activity (based on formate production) (Table 4) and low level of expression of pflB (Table 3) during growth of the mutant strains at pH 5.0 suggest that culture pH plays a role in the control of PFL. To increase the anaerobic growth rate and cell yield in pH 5.0 fermentations due to an increase in expression of ldhA and/or activity of D-LDH over that of PFL, a growth-based selection was implemented. In contrast, a similar growth-based selection of the ldh, alsS double mutant at pH 7.0 that has higher level of PFL activity could lead to derivatives with elevated level of PFL and not D-LDH.

Figure 3:
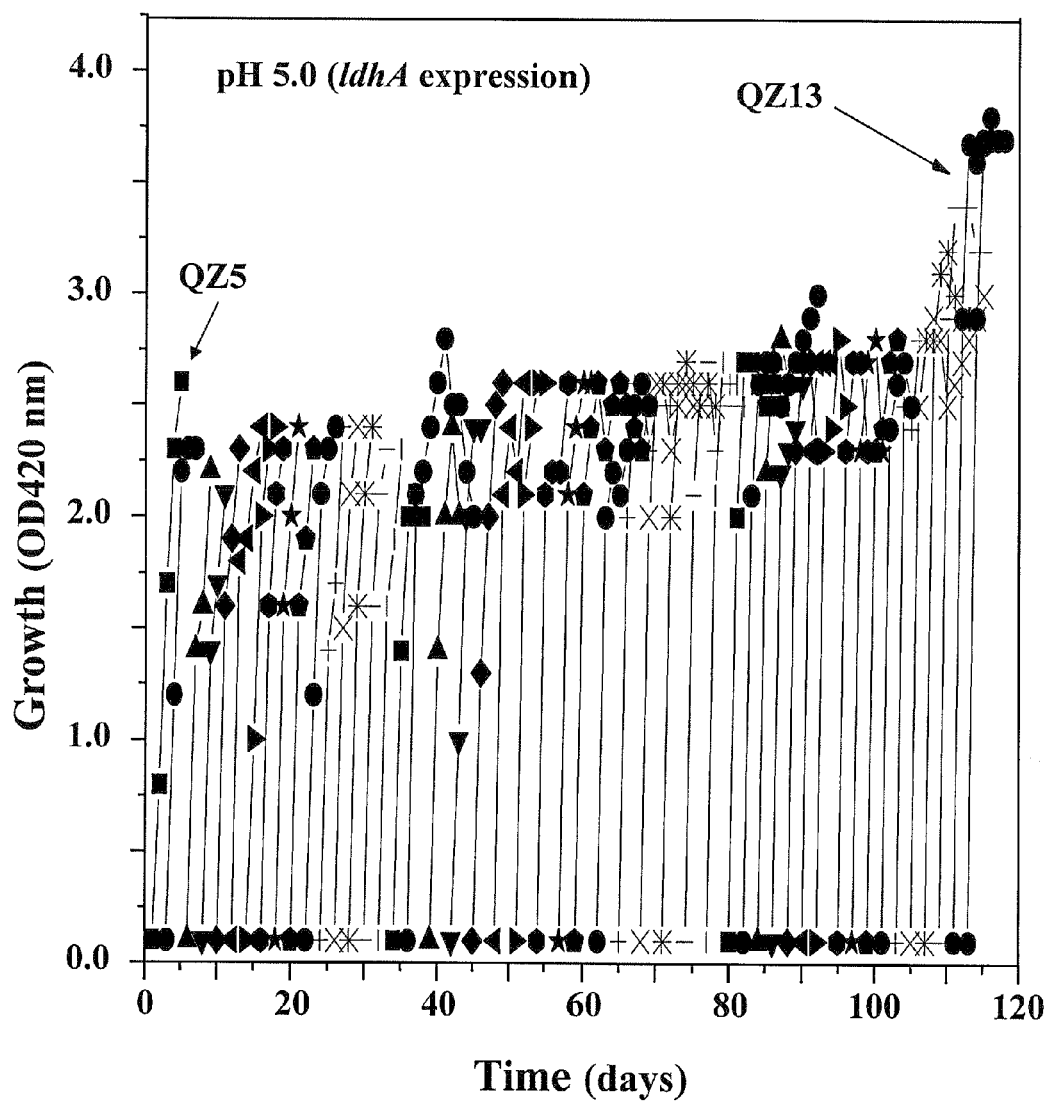
FIG. 3. Growth-based selection of *B. coagulans* strain QZ5 in small fermenters in LB+glucose (30 g/L) at pH 5.0 leading to strain QZ13.

Anaerobic growth-dependent selection of strain QZ5 at pH 5.0 in LB+glucose fermentations yielded a derivative after about 120 days (FIG. 3). This strain, QZ13, produced higher cell yield than the starting strain QZ5 in pH 5.0 fermentations. Although the cell yield and glucose consumption of strain QZ13 and its starting parent, QZ5 were about the same in pH 7.0 fermentations, the D-lactic acid yield of strain QZ13 in pH 7.0 fermentations was about 10-fold higher than the lactic acid yield of strain QZ5 at the same fermentation pH (Table 4). The PDH/PFL contribution to the fermentation products also decreased to about 0.4 of the glucose consumed from 0.85 for strain QZ5.

Figure 4:
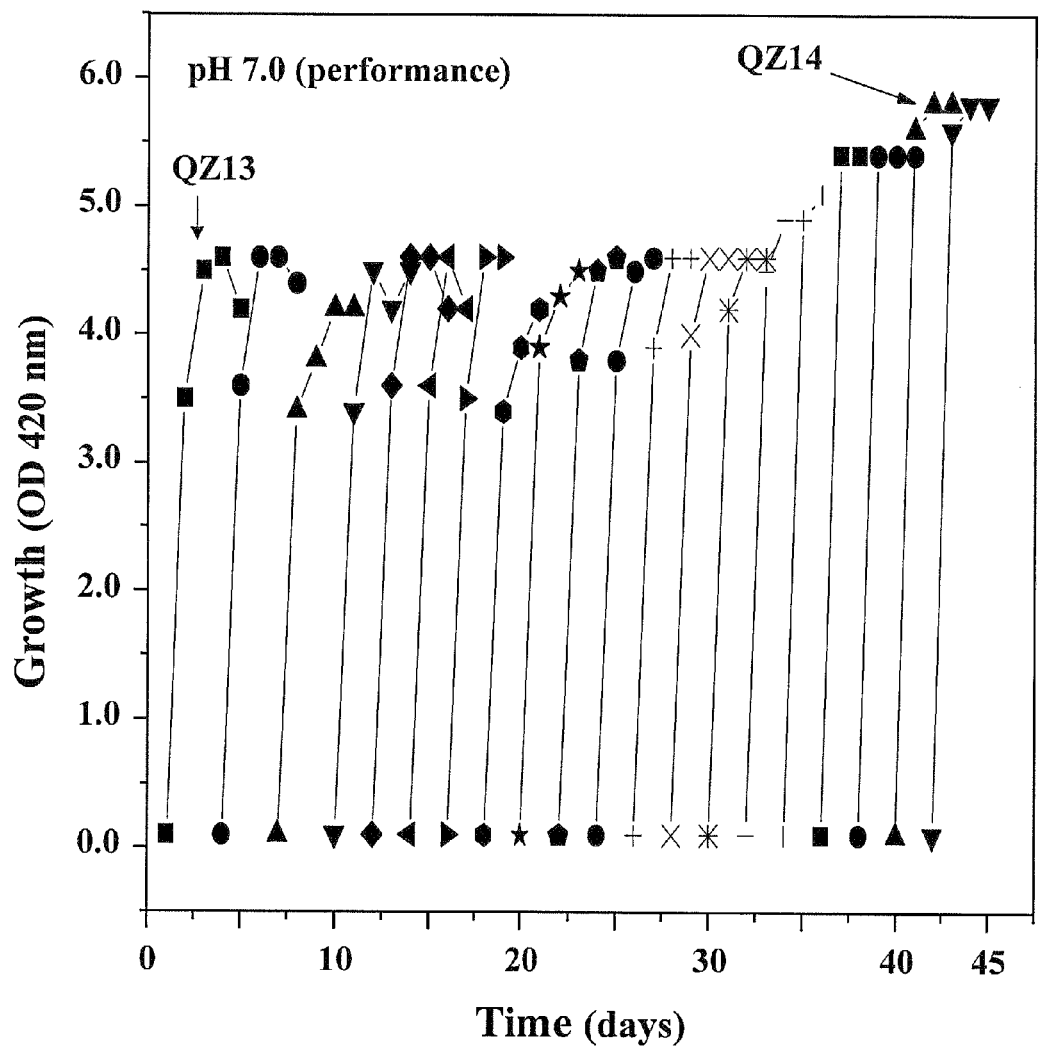
FIG. 4. Growth-based selection of *B. coagulans* strain QZ13 in small fermenters in LB+glucose (50 g/L) at pH 7.0 leading to strain QZ14.
Figure 5:
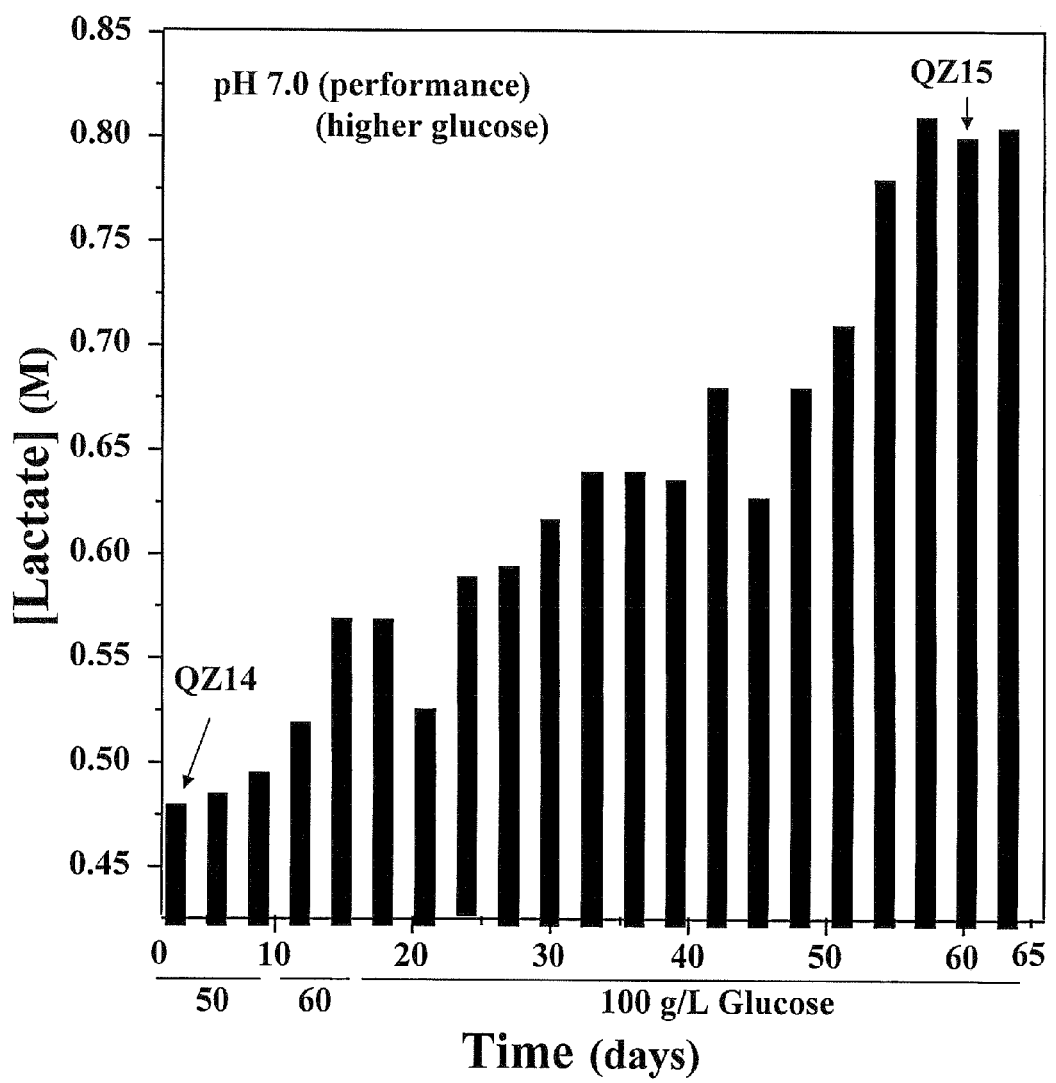
FIG. 5. Growth-based selection of *B. coagulans* strain QZ14 in small fermenters in LB+glucose at pH 7.0 with increasing glucose concentration leading to strain QZ15. Medium also contained 20 g/L $CaCO_3$. Starting glucose concentration was 50 g/L. After the third transfer glucose concentration was increased to 60 g/L. Glucose concentration of the medium was 100 g/L after the fifth transfer.
Figure 6:
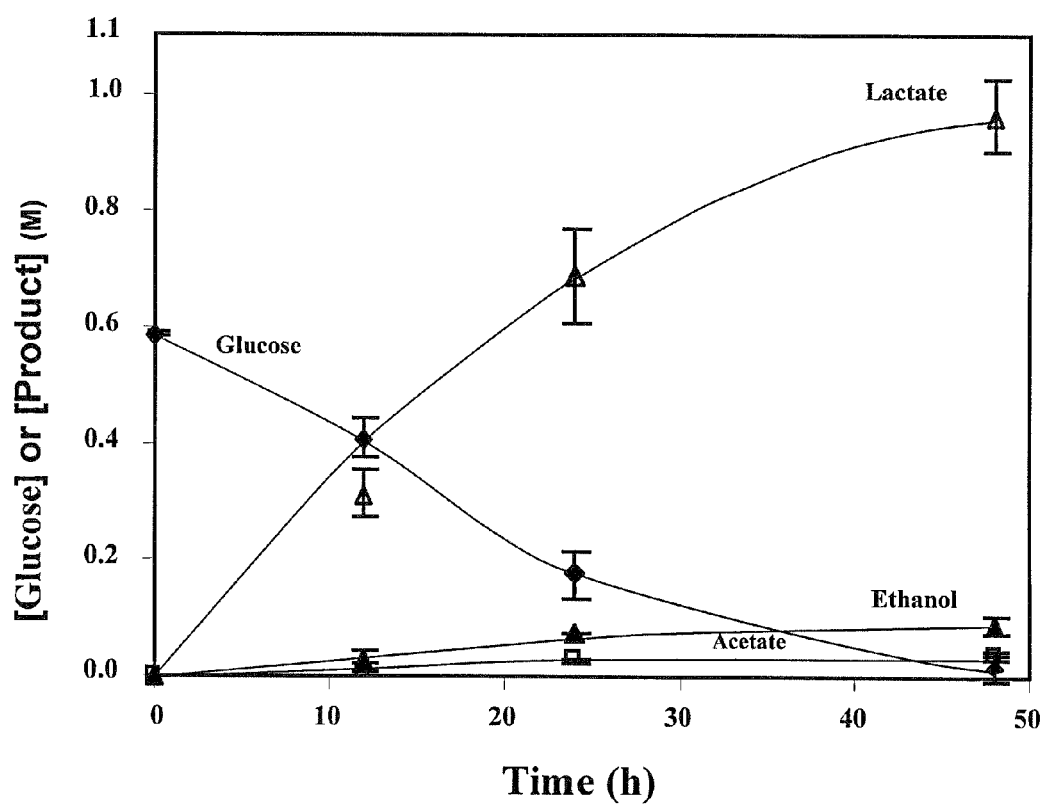
FIG. 6. Fermentation profile of *B. coagulans* strain QZ19 at pH 7.0 in LB+glucose with 20 g/L CaCO$_3$. L(+)-lactic acid or formate was not detectable in the fermentation broth.

The need to increase D-lactic acid yield with a concomitant reduction in PFL/PDH derived products in pH 7.0 fermentations of strain QZ13 led to further selection for higher growth and cell yield at pH 7.0 in LB+glucose fermentations. Strain QZ14 was derived after about 40 days of continual selection and enrichment at pH 7.0 (FIG. 4). Lactate yield of strain QZ14 was about 0.8 of the glucose fermented and the PFL/PDH contribution decreased to about 7% of the glucose derived products (Table 4). Strain QZ14 fermentation broth still contained detectable level of pyruvate, suggesting that the D-LDH level in the cell is not matching glucose flux through glycolysis. Next set of selections focused on increasing lactate titer to isolate a mutant derivative that effectively couples LDH activity to glycolytic flux of glucose. Strain QZ15 was isolated after an additional 60 days of sequential transfer and selection with increasing glucose concentration (FIG. 5). The D(−)-lactic acid titer of strain QZ15 in pH 7.0 fermentations of glucose was over 80 g/L. Continued evolution of strain QZ15 led to further increase in glucose flux to lactic acid reaching about 90 g/L in less than 48 hours of pH 7.0 fermentations (Strain QZ19; Table 4; FIG. 6). Formate was not detected in these derivatives with high lactic acid titer. The small amount of ethanol and acetate produced by these cultures is probably derived from PDH-produced acetyl-CoA (15).

These results show that by deletion of the ldh and alsS genes combined with anaerobic growth-based selection for appropriate mutations based on an understanding of the physiology of the organism at the pyruvate node can lead to alteration of the primary fermentation product of *B. coagulans* to D(−)-lactic acid from that of L(+)-lactic acid. Although the pflAB genes are still intact in the final derivative, increasing metabolic flux to D-lactate through D-LDH, essentially neutralized any pyruvate flux to acetyl-CoA through PFL. Further studies to identify the mutation(s) that led to elevated D-LDH activity in QZ19 have been conducted (the results of which have been published in an article entitled "Evolution of D-lactate dehydrogenase activity from glycerol dehydrogenase and its utility for D-lactate production from lignocellulose", Wang et al., *Proc. Natl. Acad. Sci., USA*, 2011, 108: 18920-18925 and which is hereby incorporated by reference in its entirety).

CONCLUSION

Using a method developed for deleting a specific gene in the genetically recalcitrant *B. coagulans*, the ldh gene encoding L-LDH was deleted. The Δldh mutant failed to grow anaerobically at pH 5.0 while growth at pH 7.0 was not significantly affected. PFL, PDH and 2,3-butanediol pathway supported fermentative growth at pH 7.0. Deleting ldh, alsS and pflB eliminated anaerobic growth of the mutant although a gene encoding D-LDH (ldhA) is present in the chromosome. Based on an understanding of the physiological properties of *Bacillus coagulans* at various growth pH and the flow of carbon at the pyruvate node during anaerobic growth in this bacterium, a growth-based selection starting with an ldh, alsS double mutant yielded a mutant with enhanced ability to produce D-lactic acid to levels that are comparable to the L-lactic acid yield and titer of the wild type. Further increase in the rate of lactic acid production is expected to eliminate the small amount of co-products ethanol and acetic acid present in the fermentation broth. This is the first report of a thermophilic lactic acid bacterium in which the primary fermentation product has been changed from L(+)-lactic acid to D(−)-lactic acid using only the native genes of the bacterium (without foreign gene). This is based on selective mutations and evaluation of the physiology of the bacterium that led to appropriate additional strategies. Availability of thermotolerant *B. coagulans* strains that produce optically pure D(−)- or L(+)-lactic acid at 50-55° C. is expected to help reduce the cost of lactic acid as a feedstock for production of bio-based polylactide plastics of varying thermochemical properties by minimizing potential contaminants that can lower the optical purity of lactic acid.

TABLE 1

Bacterial strains, plasmids and primers used in this study

| | Relevant genotype | Source or Reference |
|---|---|---|
| Strain | | |
| P4-102B | Wild type | (26) |
| *E. coli* Top10 | | Invitrogen |
| *B. subtilis* HB1000 | | (11) |
| QZ3 | P4-102B ldh::pQZ44, $Em^R$ | This work |
| QZ4 | QZ3 Δldh | This work |
| QZ5 | QZ4 ΔalsS | This work |
| QZ13 | QZ5 evolved at pH 5.0 for higher cell yield | This work |
| QZ14 | QZ13 evolved at pH 7.0 for higher lactic acid titer | This work |
| QZ15 | QZ14 evolved for higher sugar use | This work |
| QZ16 | QZ15 selected for higher rate of glucose use and lactate production from $CaCO_3$ medium | This work |
| QZ19 | QZ16 further evolved for higher rate of lactate production. | This work |
| plasmid | | |
| pGK12 | Broad host-range, $Cm^R$, $Em^R$ | (16) |
| pUC19 | Plasmid vector $Ap^R$ | Lab stock |
| pQZ44 | pGK12 with promoterless ldh (P4-102B) with 100 bp deletion | This work |
| pQZ 45 | pUC19 with P4-102B alsSD | This work |
| PQZ45-1 | pUC19 with 2,380 bp promoterless P4-102B alsSD | This work |
| pQZ54 | PQZ45-1 with 596 bp alsS deletion with $Em^R$ gene insertion | This work |
| pQZ64 | pGK12 with 506 bp alsS deletion with $Em^R$ gene insertion | This work |

TABLE 2

Primers used

| Primer name | Sequence(5'-3') |
|---|---|
| Primer9 | ccctacgtaTTGGAACGGGTGCAGTTGGT (SEQ ID NO: 4) |
| Primer10 | cccgaattcCCGGGTTGCTGGCAACAAGA (SEQ ID NO: 5) |
| Primer11 | cccgaattcTTTGAGCGCCCAATTTGGAA (SEQ ID NO: 6) |
| Primer12 | cccaggcctCCGGAACGCCAACGTACACA (SEQ ID NO: 7) |
| Primer17 | ACGAGCCGCTGACACTGGAT (SEQ ID NO: 8) |
| Primer18 | GCCGTCTTCGCCTTCGTTCA (SEQ ID NO: 9) |
| Primer19 | TGAACCGAACCGCCTGCTGT (SEQ ID NO: 10) |
| Primer20 | TCGCGCCAGACGATATGCAC (SEQ ID NO: 11) |
| Primer21 | TGTCATAAGTCGCCGAACCG (SEQ ID NO: 12) |
| Primer22 | TGATTGTATGCCGCCACGAA (SEQ ID NO: 13) |
| Primer23 | GGTGTTGCAGAAGAGCTTGT (SEQ ID NO: 14) |
| Primer24 | GTGCCGCAATCGGAATAATC (SEQ ID NO: 15) |

TABLE 2-continued

Primers used

| Primer name | Sequence(5'-3') |
|---|---|
| Primer25 | CATCAACGCCGCCGTTAATC (SEQ ID NO: 16) |
| Primer26 | TCGTTCCGCTTCCTGAACAC (SEQ ID NO: 17) |
| Primer27 | CCCGCCGCAAATCATTATCG (SEQ ID NO: 18) |
| Primer28 | TAAAAGCACCCGCAAAGTT (SEQ ID NO: 19) |
| Primer29 | AGATCTTAAGCCGTGTGGAG (SEQ ID NO: 20) |
| Primer30 | CGCAACAATACTGCCGATTC (SEQ ID NO: 21) |
| Primer31 | TCGCTTCCGCTCGTCGTCTT (SEQ ID NO: 22) |
| Primer32 | TCCCGCAAATCCCTTACCTG (SEQ ID NO: 23) |
| Primer33 | TTGGAGGCGAACAAAGAACA (SEQ ID NO: 24) |
| Primer34 | CGGCAATGGAAAAAGAAATG (SEQ ID NO: 25) |

Capital letters represent *B. coagulans* sequence. Lower case letters indicate the restriction enzyme recognition sequence and 5' extensions for optimum cleavage of the amplified product by the respective enzyme.

TABLE 3 mRNA level of genes encoding enzymes at the pyruvate node in *B. coagulans* wild type and Δldh mutant, strain QZ4

| Strain | Culture pH | OD 420 nm* | mRNA Level (ng/ml)** | | | | | Enzyme Activity† | |
|---|---|---|---|---|---|---|---|---|---|
| | | | pdhA | ldh‡ | pflB | alsS | ldhA‡ | PDH | LDH |
| P4-102B (wild type) | 5.0 | 1.0 | 2.73 | 61.92 | 0.02 | 0.08 | 0.12 | 0.4 | 14.0 |
| | 5.0 | 3.4 | 25.59 | 61.55 | 0.87 | 0.27 | 0.19 | 8.0 | 23.5 |
| | 7.0 | 1.0 | 2.59 | 55.11 | 0.09 | 0.14 | 0.22 | 3.8 | 29.9 |
| | 7.0 | 4.3 | 11.53 | 12.75 | 3.20 | 0.11 | 0.15 | 20.6 | 28.1 |
| Mutant QZ4 (Δldh) | 5.0 | 1.0 | 3.39 | 0.02 | 0.37 | 5.30 | 1.08 | 1.9 | 1.6 |
| | 5.0 | 2.0 | 2.76 | 0.001 | 0.57 | 1.32 | 1.95 | 6.3 | 2.2 |
| | 7.0 | 1.0 | 2.51 | 0.004 | 1.22 | 3.07 | 1.65 | 6.6 | 1.6 |
| | 7.0 | 7.0 | 33.41 | 0.21 | 2.67 | 5.62 | 0.88 | 3.1 | 2.5 |

*Represents the OD420 nm at the time of harvest. Cells were harvested from pH controlled fermentations (LB + glucose) during early to mid-exponential phase of growth (OD value of 1.0) and late-exponential phase of growth (the second OD value).
**Concentration of specific mRNA in the total isolated RNA.
†Enzyme activity was determined in crude extracts and expressed as nmoles min$^{-1}$ mg protein$^{-1}$.
‡ldh and ldhA represent the genes encoding the L(+)- and D(−)-lactate dehydrogenases, respectively.

TABLE 4

Fermentation profiles of *B. coagulans* derivatives on the path to D(−)-lactic acid production at 50° C.

| Strain | Genotype | Culture pH | Growth (OD420 nm) | Glucose Consumed (mM) | Lactate* L(+)- | D(−) | Pyruvate | Acetate | Succ | Formate | Ethanol | Yield Lac | Total |
|---|---|---|---|---|---|---|---|---|---|---|---|---|---|
| P4-102B | wild type | 5.0 | 3.0 | 144.3 | 255.6 | UD | UD | 5.7 | 0.6 | UD | 10.5 | 0.90 | 1.00 |
| | | 7.0 | 7.1 | 188.6 | 336.4 | UD | UD | 15.9 | 0.4 | UD | 4.6 | 0.89 | 0.96 |
| QZ4** | Δldh | 5.0 | 1.8 | 53.8 | UD | 1.0 | UD | UD | 1.0 | 6.5 | 20.3 | 0.01 | 0.21 |
| | | 7.0 | 8.1 | 226.0 | UD | 9.7 | UD | 42.3 | 6.7 | 90.6 | 224.5 | 0.02 | 0.63 |
| QZ5 | Δldh ΔalsD | 5.0 | 2.5 | 32.8 | UD | 9.8 | 4.5 | 4.6 | 0.1 | 25.3 | 25.6 | 0.15 | 0.72 |
| | | 7.0 | 5.8 | 152.5 | UD | 12.8 | 10.1 | 95.4 | 2.1 | 154.6 | 164.5 | 0.04 | 0.94 |
| QZ13 | Continued selection | 5.0 | 3.7 | 34.5 | UD | 20.9 | 20.9 | 2.5 | 0.4 | 15.9 | 18.8 | 0.30 | 0.92 |
| | | 7.0 | 5.1 | 148.7 | UD | 139.9 | 15.8 | 45.2 | 3.2 | 90.0 | 80.7 | 0.50 | 1.00 |
| QZ14 | Continued selection | 5.0 | | | | | | | | | | | |
| | | 7.0 | 5.8 | 199.0 | UD | 335.3 | 11.4 | 5.7 | 0.5 | 44.0 | 39.0 | 0.80 | 0.99 |
| | | 7.0† | | 265.7 | UD | 468.4 | 1.6 | UD | 1.3 | 21.5 | 28.4 | 0.88 | 0.93 |
| QZ15 | Continued selection | 7.0† (68 h) | | 562.6 | UD | 928.2 | UD | 22.6 | 8.1 | UD | 97.5 | 0.83 | 0.94 |
| QZ19 | | 7.0† (48 h) | | 590.0 | UD | 993.0 | UD | 45.3 | 5.7 | UD | 84.2 | 0.84 | 0.96 |

All fermentations were in LB medium with glucose and the reported values were after 72 h, unless indicated otherwise.
*Values in parenthesis indicate that both isomers were present.
**Strain QZ4 also produced acetoin and 2,3-butanediol; pH 5.0 culture, 44.5 mM 2,3-butanediol; pH 7.0 culture, 31.6 mM acetoin and 93.1 mM 2,3-butanediol. These two products were not detected in the broths from other cultures.
†Due to the presence of CaCO$_3$ in the medium, the cell density of these cultures was not determined.
UD—undetectable
Succ, succinate; Lac, lactate

TABLE 5

| Culture | Strain Designations | Deposit Date |
|---|---|---|
| QZ4 | NRRL B-50438 | Nov. 4, 2010 |
| QZ5 | NRRL B-50439 | Nov. 4, 2010 |
| QZ13 | NRRL B-50440 | Nov. 4, 2010 |
| QZ14 | NRRL B-50441 | Nov. 4, 2010 |
| QZ15 | NRRL B-50442 | Nov. 4, 2010 |
| QZ19 | NRRL B-50443 | Nov. 4, 2010 |

REFERENCES

1. Abdel-Banat B M A, Hoshida H, Ano A, Nonklang S, Akada R (2010) High-temperature fermentation: how can process for ethanol production at high temperatures become superior to the traditional process using mesophilic yeast? Appl Microbiol Biotechnol 85:861-867.
2. Beall D S, Ohta K, Ingram L O (1991) Parametric studies of ethanol production from xylose and other sugars by recombinant *Escherichia coli*. Biotechnol Bioeng 38:296-303.
3. Benninga H 1990. A history of lactic acid making. Kluyver Academic Publishers, Dordrecht, the Netherlands.
4. Boylan R J, Mendelson N H, Brooks D, Young F E (1972) Regulation of the bacterial cell wall: analysis of a mutant of *Bacillus subtilis* defective in biosynthesis of teichoic acid. J Bacteriol 110:281-290.
5. Bradford M M (1976) A rapid and sensitive method for the quantitation of microgram quantities of protein utilizing the principle of protein-dye binding. Anal Biochem 72:248-254.
6. Can F J, Chill D, Maida N (2002) The lactic acid bacteria: A literature survey. Crit Rev Microbiol 28:281-370.
7. Datsenko K A, Wanner B L (2000) One-step inactivation of chromosomal genes in *Escherichia coli* K-12 using PCR products. Proc Natl Acad Sci USA 97:6640-6645.
8. Datta R, Henry M (2006) Lactic acid: recent advances in products, processes and technologies—a review. J Chem Technol Biotechnol 81:1119-1129.
9. Davis R W, Botstein D, Roth J R 1980. Advanced Bacterial Genetics. Cold Spring Harbor Laboratory, Cold Spring Harbor, N.Y.
10. De Clerck E, Rodriguez-Diaz M, Forsyth G, Lebbe L, Logan N A, DeVos P (2004) Polyphasic characterization of *Bacillus coagulans* strains, illustrating heterogeneity within this species, and emended description of the species. System Appl Microbiol 27:50-60.
11. Fredrick K, Heimann J D (1996) FlgM is a primary regulator of sigmaD activity, and its absence restores motility to a sinR mutant. J Bacteriol 178:7010-7013.
12. Grabar T B, Zhou S, Shanmugam K T, Yomano L P, Ingram L O (2006) Methylglyoxal bypass identified as source of chiral contamination in L(+) and D(−)-lactate fermentations by recombinant *Escherichia coli*. Biotechnol Lett 28:1527-1535,
13. Hamilton C M, Aldea M, Washburn B K, Babitzke P, Kushner S R (1989) New method for generating deletions and gene replacements in *Escherichia coli*. J Bacteriol 171:4617-4622.
14. Hofvendahl K, Hans-Hagerdal B (2000) Factors affecting the fermentative lactic acid production from renewable resources. Enz Microb Technol 26:87-107.
15. Kim Y, Ingram L O, Shanmugam K T (2007) Construction of an *Escherichia coli* K-12 mutant for homoethanologenic fermentation of glucose or xylose without foreign genes. Appl Environ Microbiol 73:1766-1771,
16. Kim Y, Ingram L O, Shanmugam K T (2008) Dihydrolipoamide dehydrogenase mutation alters the NADH sensitivity of pyruvate dehydrogenase complex of *Escherichia coli* K-12. J Bacteriol 190:3851-3858.
17. Kok J, van der Vossen J M, Venema G (1984) Construction of plasmid cloning vectors for lactic streptococci which also replicate in *Bacillus subtilis* and *Escherichia coli*. Appl Environ Microbiol 48:726-731.
18. Kulkarni R K, Moore E G, Hegyeli A F, Leonard F (1971) Biodegradable poly(lactic acid) polymers. J Biomed Mater Res 5:169-181.
19. Lee J H, Patel P, Sankar P, Shanmugam K T (1985) Isolation and characterization of mutant strains of *Escherichia coli* altered in $H_2$ metabolism. J Bacteriol 162:344-352.
20. Lin Y, Hansen J N (1995) Characterization of a chimeric proU operon in a subtilin-producing mutant of *Bacillus subtilis* 168. J Bacteriol 177:6874-6880.
21. Luchansky J B, Muriana P M, Klaenhammer T R (1988) Application of electroporation for transfer of plasmid DNA to *Lactobacillus, Lactococcus, Leuconostoc, Listeria, Pediococcus, Bacillus, Staphylococcus, Enterococcus* and *Propionibacterium*. Mol Microbiol 2:637-646.
22. Matsumoto K, Taguchi S Enzymatic and whole-cell synthesis of lactate-containing polyesters: toward the complete biological production of polylactate. Appl Microbiol Biotechnol 85:921-932.
23. Mecking S (2004) Nature or petrochemistry?-biologically degradable materials. Angew Chem Int Ed 43:1078-1085.
24. Morimoto T, Kadoya R, Endo K. Tohata M, Sawada K, Liu S, Ozawa T, Kodama T, Kakeshita H, Kageyama Y, Manabe K, Kanaya S, Ara K, Ozaki K, Ogasawara N (2008) Enhanced recombinant protein productivity by genome reduction in *Bacillus subtilis*. DNA Research 15:73-81.
25. Okano K, Yoshida S, Yamada R, Tanaka T, Ogino C, Fukuda H, Kondo A (2009) Improved production of homo-D-lactic acid via xylose fermentation by introduction of xylose assimilation genes and redirection of the phosphoketolase pathway to the pentose phosphate pathway in L-Lactate dehydrogenase gene-deficient *Lactobacillus plantarum*. Appl Environ Microbiol 75:7858-7861.
26. Ou M S, Ingram L O, Shanmugam K T (2011) L: (+)-Lactic acid production from non-food carbohydrates by thermotolerant *Bacillus coagulans*. J Ind Microbiol Biotechnol. 38: 599-605.
27. Patel M A, Ou M S, Harbrucker R, Aldrich H C, Buszko M L, Ingram L O, Shanmugam K T (2006) Isolation and characterization of acid-tolerant, thermophilic bacteria for effective fermentation of biomass-derived sugars to lactic acid. Appl Environ Microbiol 72:3228-3235.
28. Payot T, Chemaly Z, Fick M (1999) Lactic acid production by *Bacillus coagulans*-Kinetic studies and optimization of culture medium for batch and continuous fermentations. Enz Microb Technol 24:191-199.
29. Rhee M S, Kim J W, Qian Y, Ingram L O, Shanmugam K T (2007) Development of plasmid vector and electroporation condition for gene transfer in sporogenic lactic acid bacterium, *Bacillus coagulans*. Plasmid 58:13-22.
30. Su Y, Rhee M S, Ingram L O, Shanmugam K T (2011) Physiological and fermentation properties of *Bacillus coagulans* and a mutant lacking fermentative lactate dehydrogenase activity. J Ind Microbiol Biotechnol. 1.38:441-450.
31. Tanaka K, Komiyama A, Sonomoto K, Ishizaki A, Hall S J, Stanbury P E (2002) Two different pathways for D-xylose metabolism and the effect of xylose concentration on the yield coefficient of L-lactate in mixed-acid fermentation by the lactic acid bacterium *Lactococcus lactis* 10-1. Appl Microbiol Biotechnol 60:160-167.

32. Underwood S A, Zhou S, Causey T B, Yomano L P, Shanmugam K T, Ingram L O (2002) Genetic changes to optimize carbon partitioning between ethanol and biosynthesis in ethanologenic *Escherichia coli*. Appl Environ Microbiol 68:6263-6272.

33. Visser J, Kester H, Jeyaseelan K, Topp R (1982) Pyruvate dehydrogenase complex from *Bacillus*. Methods Enzymol 89 Pt D:399-407.

34. Yanez R, Moldes A B, Alonso J L, Parajo J C (2003) Production of D(-)-lactic acid from cellulose by simultaneous saccharification and fermentation using *Lactobacillus coryniformis* subsp. *torquens*. Biotechnol Lett 25:1161-1164.

35. Yoshida A, Freese E (1975) Lactate dehydrogenase from *Bacillus subtilis*. Meth Enzymol 41:304-309.

36. Zhou S, Shanmugam K T, Ingram L O (2003) Functional replacement of the *Escherichia coli* D-(-)-lactate dehydrogenase gene (ldhA) with the L-(+)-lactate dehydrogenase gene (ldhL) from *Pediococcus acidilactici*. Appl Environ Microbiol 69:2237-2244.

We claim:

1. An isolated genetically modified *Bacillus* bacterial cell comprising the following genetic modifications and producing D(−)-lactic acid in amounts of at least 60 g/L of culture medium:
   (i) inactivation or deletion of the L(+)-lactate dehydrogenase gene; and
   (ii) inactivation or deletion of the acetolactate synthase gene.

2. The bacterial cell according to claim 1, further comprising inactivation or deletion of one or more genes encoding polypeptides selected from the group consisting of: pyruvate formate lyase, pyruvate formate lyase activating enzyme, alpha-acetolactate decarboxylase, pyruvate dehydrogenase and alcohol dehydrogenase.

3. The bacterial cell according to claim 1, further comprising genetic modifications introducing exogenous genes into said bacterial cell.

4. The bacterial cell according to claim 1, further comprising inactivation or deletion of genes encoding pyruvate formate lyase (pflB), pyruvate formate lyase activating enzyme (pflA), and alpha-acetolactate decarboxylase (alsD).

5. The bacterial cell according to claim 4, wherein the inactivation of said genes comprises the introduction of one or more point mutation(s), the introduction of one or more deletions, or the introduction of one or more stop codon(s) in the open reading frame of the gene.

6. The bacterial cell according to claim 3, wherein said genetic modification comprises insertion of an exogenous sequence into the coding region of lactate dehydrogenase, pyruvate formate lyase and/or acetolactate synthase.

7. The bacterial cell according to claim 1, wherein said bacterial cell does not contain exogenous genes or portions thereof.

8. The bacterial cell according to claim 1, wherein said bacterial cell enzymatic activity of lactate dehydrogenase, pyruvate formate lyase and/or acetolactate synthase is inactivated by homologous recombination, optionally using a plasmid sensitive to temperature.

9. The bacterial cell according to claim 8, wherein said genetic modification comprises complete or partial deletion of the gene encoding acetolactate synthase.

10. The bacterial cell according to claim 1, wherein said *Bacillus* bacterial cell is selected from the group consisting of *Bacillus coagulans, Bacillus licheniformis, Bacillus subtilis, Bacillus amyloliquifaciens, Bacillus pumilus, Bacillus circulars* or *Bacillus thiaminolyticus*.

11. A genetically modified bacterial cell selected from NRRL B-50438 (QZ4), NRRL B-50439 (QZ5), NRRL B-50440 (QZ13), NRRL B-50441 (QZ14), NRRL B-50442 (QZ15) or NRRL B-50443 (QZ19).

12. A method of producing D(−)-lactic acid comprising culturing a genetically modified bacterial cell according to claim 1 in a medium comprising a carbon source under conditions that allow for the production of D(−)-lactic acid, wherein said genetically modified bacterial cell is selected from:
   a) a genetically modified bacterial cell according to claim 1; or
   b) NRRL B-50438 (QZ4), NRRL B-50439 (QZ5), NRRL B-50440 (QZ13), NRRL B-50441 (QZ14), NRRL B-50442 (QZ15) or NRRL B-50443 (QZ19).

13. The method according to claim 12, further comprising isolating or purifying the D(−)-lactic acid.

14. The method according to claim 13, wherein said bacterial strain is cultured under anaerobic conditions.

15. The method according to claim 12, wherein said medium comprises between 2% and 20% (w/v) carbon source.

16. The method according to claim 12, wherein the carbon source is glucose, fructose, xylose, arbinose, galactose, mannose, rhamnose, sucrose, cellobiose, hemicelluloses, cellulose, glycerol or combination thereof.

17. The method according to claim 12, wherein said fermentation is conducted under anaerobic conditions at a pH of:
   a) about 5.0 to about 7.5; or
   b) about 7.0; or
   c) about 5.0.

18. The method according to claim 12, wherein said genetically modified bacterial cell produces at least 60 g of lactic acid per liter of fermentation medium within 48 hours of the start of fermentation.

19. The method according to claim 12, wherein the pH of medium used to culture said genetically modified bacterial cell is maintained by the automatic addition of acid or base.

20. The method according to claim 12, wherein the method comprises culturing the bacterial cell at a temperature between about 30° C. and about 65° C.; between about 37° C. and about 65° C.; between about 37° C. and about 55° C.; between about 45° C. and about 60° C.; between about 45° C. and about 50° C.; or at a temperature of about 30° C.; about 37° C.; or about 55° C.

21. The bacterial cell according to claim 1, further comprising inactivation or deletion of genes encoding, pyruvate formate lyase (pflB) and alpha-acetolactate decarboxylase (alsD).

22. The bacterial cell according to claim 1, further comprising inactivation or deletion of genes encoding pyruvate formate lyase (pflB), pyruvate formate lyase activating enzyme (pflA), and alpha-acetolactate decarboxylase (alsD).

23. The bacterial cell according to claim 1, wherein said bacterial cell produces D(−)-lactic acid in amounts of at least 70 g/L of culture medium.

24. The bacterial cell according to claim 1, wherein said bacterial cell produces D(−)-lactic acid in amounts of at least 80 g/L of culture medium.

* * * * *

UNITED STATES PATENT AND TRADEMARK OFFICE
CERTIFICATE OF CORRECTION

PATENT NO. : 8,900,835 B2  Page 1 of 1
APPLICATION NO. : 13/301836
DATED : December 2, 2014
INVENTOR(S) : Qingzhao Wang, Keelnatham T. Shanmugam and Lonnie O. Ingram It is certified that error appears in the above-identified patent and that said Letters Patent is hereby corrected as shown below:

In the Specification

Column 15,
Line 67, "(c=6,220" should read --($\varepsilon$ = 6,220--.

Column 20,
Line 30, "PQZ45-1" should read --pQZ45-1--.
Line 32, "PQZ45-1 with 596 bp alsS" should read --pQZ45-1 with 596 bp alsS--.

Column 23,
Line 33, "Can F J," should read --Carr FJ,--.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 25

<210> SEQ ID NO 1
<211> LENGTH: 2300
<212> TYPE: DNA
<213> ORGANISM: Bacillus coagulans
<220> FEATURE:
<221> NAME/KEY: exon
<222> LOCATION: (851)..(1789)
<223> OTHER INFORMATION: Open reading frame (ORF) ldh (L-Lactate
      dehydrogenase)

<400> SEQUENCE: 1
ttaaggataa aatgcgaacg attgaaagtc aatgatgaat atcattcgtg tttttaatgt      60
ggcaagtacc ggaaatggaa agaaaagaat tggcagtgaa accgttctct tcttctttga     120
taataaatga aagcagccgg tatggaaaga aaaaatttac ttatataaaa ttgattttat     180
ggccggcttt attatgcccg tcgtactggc tgtccgcacg gtgtccattt atgatgcaga     240
catgaatggc tgggcagttg cgttttttgtc gatgcctggc gtgcacgcct ccatgcatgt     300
gaagcgggtt tttttaagcg ggcagcaccc gcttttttgg agggcaggca ttcaggagca     360
aaaatggcag agatcatttg ggcgggatca gccatttatt cctccatccg gggcactttg     420
tgaaaatcag cacaagaatg aataacgctt acatatctgg ctctttcaaa taaagccatt     480
tgtgaaaaat gtaaacggat aattttgaaa aaccgtcatt ttcctttaaa accgggcatt     540
tgggcagata aattttcaaa ttttcgccat aaaatatgtg aatctgatca caaaaatagt     600
ggtatactta cccatgtgga atgaaggaaa atgaacggaa cagtcaattt cagccataaa     660
gggcatgccg tccatctatt tcacaaaccg cacggcagca ttgctgcaaa gtttaattgt     720
cctgctttaa aggaaagcag tatggatcca ttaggagtttg cacatatcca tagactggat     780 agggcccgc atgccgggct gcaaactgct ttcatacagt gatatatttt tacttgatgg     840
agagatatac atg aaa aag gtc aat cgt att gca gtg gtt gga acg ggt          889
            Met Lys Lys Val Asn Arg Ile Ala Val Val Gly Thr Gly
              1               5                  10 gca gtt ggt aca agt tac tgc tac gcc atg att aat cag ggt gtt gca         937
Ala Val Gly Thr Ser Tyr Cys Tyr Ala Met Ile Asn Gln Gly Val Ala
         15                  20                  25 gaa gag ctt gtt tta atc gat att aac gaa gca aaa gca gaa ggg gaa         985
Glu Glu Leu Val Leu Ile Asp Ile Asn Glu Ala Lys Ala Glu Gly Glu
 30                  35                  40                  45 gcc atg gac ctg aac cac ggc ctg cca ttt gcg cct acg ccg acc cgc        1033
Ala Met Asp Leu Asn His Gly Leu Pro Phe Ala Pro Thr Pro Thr Arg
             50                  55                  60 gtt tgg aaa ggc gat tat tcc gat tgc ggc act gcc gat ctt gtt gtc       1081
Val Trp Lys Gly Asp Tyr Ser Asp Cys Gly Thr Ala Asp Leu Val Val
         65                  70                  75
```

```
att acg gca ggt tcc ccg caa aaa ccg ggc gaa aca agg ctt gat ctt      1129
Ile Thr Ala Gly Ser Pro Gln Lys Pro Gly Glu Thr Arg Leu Asp Leu
        80                  85                  90 gtt gcc aaa aac gca aaa att ttt aaa ggc atg att aag agc atc atg      1177
Val Ala Lys Asn Ala Lys Ile Phe Lys Gly Met Ile Lys Ser Ile Met
 95                 100                 105 gac agc ggc ttt aac ggg att ttt ctt gtt gcc agc aac ccg gtt gac      1225
Asp Ser Gly Phe Asn Gly Ile Phe Leu Val Ala Ser Asn Pro Val Asp
110                 115                 120                 125 att ttg aca tat gta act tgg aaa gag tcc ggc ctg ccg aaa gaa cat      1273
Ile Leu Thr Tyr Val Thr Trp Lys Glu Ser Gly Leu Pro Lys Glu His
            130                 135                 140 gtt atc ggt tcg ggc aca gtg ctt gac tcc gcg cgt ctc cgc aac tct      1321
Val Ile Gly Ser Gly Thr Val Leu Asp Ser Ala Arg Leu Arg Asn Ser
                145                 150                 155 ttg agc gcc caa ttt gga att gac ccg cgc aat gtg cat gct gcg att      1369
Leu Ser Ala Gln Phe Gly Ile Asp Pro Arg Asn Val His Ala Ala Ile
            160                 165                 170 atc ggc gaa cac ggc gat acg gaa ctt ccg gta tgg agc cat aca aat      1417
Ile Gly Glu His Gly Asp Thr Glu Leu Pro Val Trp Ser His Thr Asn
175                 180                 185 atc ggt tac gat acg att gaa agc tat cta caa aaa gga att att gac      1465
Ile Gly Tyr Asp Thr Ile Glu Ser Tyr Leu Gln Lys Gly Ile Ile Asp
190                 195                 200                 205 gaa aag acg tta gat gac att ttt gtc aat acg aga gat gcg gct tat      1513
Glu Lys Thr Leu Asp Asp Ile Phe Val Asn Thr Arg Asp Ala Ala Tyr
            210                 215                 220 cat att att gaa cga aaa ggg gcc aca ttt tac ggc atc ggg atg tcc      1561
His Ile Ile Glu Arg Lys Gly Ala Thr Phe Tyr Gly Ile Gly Met Ser
                225                 230                 235 ctg acc cgg att aca agg gca atc ctg aac aat gaa aac agc gta ttg      1609
Leu Thr Arg Ile Thr Arg Ala Ile Leu Asn Asn Glu Asn Ser Val Leu
            240                 245                 250 acg gtc tct gca ttt ctt gaa ggc caa tac gga aac agc gat gtg tac      1657
Thr Val Ser Ala Phe Leu Glu Gly Gln Tyr Gly Asn Ser Asp Val Tyr
255                 260                 265 gtt ggc gtt ccg gcc atc atc aat cgc cag ggc atc cgt gaa gtg gtt      1705
Val Gly Val Pro Ala Ile Ile Asn Arg Gln Gly Ile Arg Glu Val Val
270                 275                 280                 285 gaa atc aaa ctg aac gaa aaa gaa cag gaa cag ttc aat cat tct gta      1753
Glu Ile Lys Leu Asn Glu Lys Glu Gln Glu Gln Phe Asn His Ser Val
            290                 295                 300 aaa gtg cta aaa gaa aca atg gca ccg gta ttg taa gcatttgtgc           1799
Lys Val Leu Lys Glu Thr Met Ala Pro Val Leu
                305                 310 cggccgggct tcatgggagg cccggctttt tctttgaaaa aaatcccggc gcctgcttaa    1859
ggcggactgc cgaaaaaagt gcccatgctt gccccgcttt ccgggaaaag catgggcctg    1919
ttttttgccg gggttaggag ggggcctgcc ataggcggat ataaaaaagc agccttgaat    1979
cgattcaagg ctgcttttc ttaattcaat atgatcactt tgaccgtacg gcgcccccat     2039
gcgatggaag ctttttgtt cggcatcagg acatcgatga tatggccctt aatggcaccg     2099
ccggtatcgg ctgcgatggc aaccccgtat ccttcaaccc agactttgct gccgagcgga    2159
atgaccgatg gatcgacagc gatcaatttc atgttcgggt ttttcttaat gttatatccc    2219
aaagcggtaa tatccagctt cgtatcttca tggttataag atgtcgccgt cacataaaag    2279
gatttgcctt gtggcgtgct g                                              2300
```

```
<210> SEQ ID NO 2
<211> LENGTH: 3298
<212> TYPE: DNA
<213> ORGANISM: Bacillus coagulans
<220> FEATURE:
<221> NAME/KEY: exon
<222> LOCATION: (519)..(2207)
<223> OTHER INFORMATION: Open reading frame (ORF) alsS (acetolactate
      synthase (catabolic))
<220> FEATURE:
<221> NAME/KEY: exon
<222> LOCATION: (2292)..(3041)
<223> OTHER INFORMATION: Open reading frame (ORF) alsD
      (alpha-acetolactate decarboxylase)

<400> SEQUENCE: 2
atagccggca aaatgtcata agtcgccgaa ccgacaaagc cgactaccac attcccgaat      60 tcccccgct cagcccgctg tgcattttcc ctgccctgtc cagctgctca aggacctgct     120
tggcctcttt taaaaaaact tttcccggga tcgtcagttc aacatgacgt ttattgcgga    180
taaaaaggtc caccccgatt tcttcttcca gctgccggat ttgctgggaa agcggtggct    240
gggtcatttg cagccgctct gctgcttttc cgaaatgtag ttcttccgcg accgttaaaa    300
aataatgaag atggcgcagt tccatctgta tttcctcctc cctcattggg attaatattt    360
attatatatt atttatagca caataatata ttttaaacat ttcctcgtgt ggtgtaaagt    420
atagatagaa acaagttcgc tcagcctata gatgaacgtt ttccctgta ataacgggg     480 gaaagttcaa aataggctg tccttgggag tgggaact gtg gaa aaa aag aat tca    536
                                          Val Glu Lys Lys Asn Ser
                                           1               5 aat cca acc aat acg acg aaa aaa aca gct gca gac ctg gtt gtc gat     584
Asn Pro Thr Asn Thr Thr Lys Lys Thr Ala Ala Asp Leu Val Val Asp
         10                  15                  20 tgc ctt gaa aaa cag gaa gtt ccg tac gtt ttc ggc att ccg ggc gca     632
Cys Leu Glu Lys Gln Glu Val Pro Tyr Val Phe Gly Ile Pro Gly Ala
     25                  30                  35 aaa atc gat gcc gta ttt gat gtc cta aaa gaa cgc ggc ccg gaa ttg     680
Lys Ile Asp Ala Val Phe Asp Val Leu Lys Glu Arg Gly Pro Glu Leu
 40                  45                  50 att gta tgc cgc cac gaa caa aat gcc gct ttt atg gcc gct gct atc     728
Ile Val Cys Arg His Glu Gln Asn Ala Ala Phe Met Ala Ala Ala Ile
 55                  60                  65                  70 ggg cgt tta aca gga aaa ccg ggt gtc tgc ctg gta acg agc ggg ccg     776
Gly Arg Leu Thr Gly Lys Pro Gly Val Cys Leu Val Thr Ser Gly Pro
                 75                  80                  85 ggg gct tcc aac ctt gcc acc ggg ctt gcc act gcg aat acg gag tgc     824
Gly Ala Ser Asn Leu Ala Thr Gly Leu Ala Thr Ala Asn Thr Glu Cys
             90                  95                 100 gat cct gtc gtt gca atc gca gga aac gtg ccg cgc gca gac aga ctg     872
Asp Pro Val Val Ala Ile Ala Gly Asn Val Pro Arg Ala Asp Arg Leu
        105                 110                 115 aaa aaa acg cac cag tcg atg gac aat gta tcc ctg ttt cag ccg att     920
Lys Lys Thr His Gln Ser Met Asp Asn Val Ser Leu Phe Gln Pro Ile
    120                 125                 130 aca aaa tac gca gcg gaa gtg gtt cat ccg gat aca gtg ccg gaa gtg     968
Thr Lys Tyr Ala Ala Glu Val Val His Pro Asp Thr Val Pro Glu Val
135                 140                 145                 150 atg aca aat gca ttt cgt tct gcc gct tca gca cag gca ggg gca gct    1016
Met Thr Asn Ala Phe Arg Ser Ala Ala Ser Ala Gln Ala Gly Ala Ala
                155                 160                 165 ttt atc agc ttc ccg cag gat gtg ctg atg gag ccg gcg tct gtc aaa    1064
Phe Ile Ser Phe Pro Gln Asp Val Leu Met Glu Pro Ala Ser Val Lys
```

```
                        170                 175                 180
gct ttg ggt ccg ctt gaa agc ccg gaa ctc ggg aaa gca aat gaa gaa        1112
Ala Leu Gly Pro Leu Glu Ser Pro Glu Leu Gly Lys Ala Asn Glu Glu
            185                 190                 195 gcg att aaa gaa gct gta aaa gcg atc cag cat gcc aaa ttg ccg gtc        1160
Ala Ile Lys Glu Ala Val Lys Ala Ile Gln His Ala Lys Leu Pro Val
200                 205                 210 att ctg gtc ggg atg cgt gcg agc cgc ccg aaa gtc gtg aaa gcg gtc        1208
Ile Leu Val Gly Met Arg Ala Ser Arg Pro Lys Val Val Lys Ala Val
215                 220                 225                 230 cgg tcc ctc ctg aaa aaa atc gca ttg ccg gtt gtt gaa aca ttc cag        1256
Arg Ser Leu Leu Lys Lys Ile Ala Leu Pro Val Val Glu Thr Phe Gln
            235                 240                 245 gcg gca ggc ttg att tca aga gat ttg gaa gac cgt ttc ttc ggc cgc        1304
Ala Ala Gly Leu Ile Ser Arg Asp Leu Glu Asp Arg Phe Phe Gly Arg
            250                 255                 260 atc ggc ttg ttc cgc aac cag ccg ggc gat att ttg ctt gag cat gcg        1352
Ile Gly Leu Phe Arg Asn Gln Pro Gly Asp Ile Leu Leu Glu His Ala
            265                 270                 275 gat gtg gtg ctt gcg atc ggt tac gat tct gtt gag tac gat ccg aag        1400
Asp Val Val Leu Ala Ile Gly Tyr Asp Ser Val Glu Tyr Asp Pro Lys
280                 285                 290 ttt tgg aac agc gaa ggg gaa aga aaa atc atc cat ctc gat gaa atc        1448
Phe Trp Asn Ser Glu Gly Glu Arg Lys Ile Ile His Leu Asp Glu Ile
295                 300                 305                 310 cgc gcc gat atc gat cat gat tac cag ccg gaa atc gaa ctt gtc ggt        1496
Arg Ala Asp Ile Asp His Asp Tyr Gln Pro Glu Ile Glu Leu Val Gly
                315                 320                 325 gac att tca gcg agc gtt gac agc atc aaa gaa cag ctg gcc cgt tta        1544
Asp Ile Ser Ala Ser Val Asp Ser Ile Lys Glu Gln Leu Ala Arg Leu
            330                 335                 340 aat atg agc agt aag tcc atg gaa ctt ttg gaa cat ctc cgc aac cag        1592
Asn Met Ser Ser Lys Ser Met Glu Leu Leu Glu His Leu Arg Asn Gln
            345                 350                 355 ctg aat ttg cgc gac gaa cca tcg gaa aag gcg gat aaa aat ctt gtg        1640
Leu Asn Leu Arg Asp Glu Pro Ser Glu Lys Ala Asp Lys Asn Leu Val
            360                 365                 370 cat ccg ctc cag ttc att cat gat ttg cgt tcg ttg att gat gac cat        1688
His Pro Leu Gln Phe Ile His Asp Leu Arg Ser Leu Ile Asp Asp His
375                 380                 385                 390 gtg acc gtg aca tgc gat gtc ggt tcc cat tat att tgg atg gcg cgc        1736
Val Thr Val Thr Cys Asp Val Gly Ser His Tyr Ile Trp Met Ala Arg
                395                 400                 405 cat ttc agg gta tat gaa ccg aac cgc ctg ctg ttt tca aat ggc atg        1784
His Phe Arg Val Tyr Glu Pro Asn Arg Leu Leu Phe Ser Asn Gly Met
            410                 415                 420 cag acg ctc ggg gtt gcg ctt ccg tgg gcg att gcc gca acg ctt gtc        1832
Gln Thr Leu Gly Val Ala Leu Pro Trp Ala Ile Ala Ala Thr Leu Val
            425                 430                 435 aat ccg gat gaa aaa gta ata tcg atc tcc gga gac ggc ggc ttc ctg        1880
Asn Pro Asp Glu Lys Val Ile Ser Ile Ser Gly Asp Gly Gly Phe Leu
            440                 445                 450 ttc tcc gcc atg gaa ctt gaa acg gcc gtc cgt tta aaa tca ccg ctt        1928
Phe Ser Ala Met Glu Leu Glu Thr Ala Val Arg Leu Lys Ser Pro Leu
455                 460                 465                 470 gtg cat atc gtc tgg cgc gac ggc acg tat gac atg gtg gcg ttc cag        1976
Val His Ile Val Trp Arg Asp Gly Thr Tyr Asp Met Val Ala Phe Gln
                475                 480                 485 cag caa atg aaa tac ggg cgc aca tcg gga gca gac ttc ggc ccc gtt        2024
```

```
                Gln Gln Met Lys Tyr Gly Arg Thr Ser Gly Ala Asp Phe Gly Pro Val
                            490                 495                 500 gat att gta aaa cac gcg gaa agt tac ggc gca aaa ggc ttg cgg gtg             2072
Asp Ile Val Lys His Ala Glu Ser Tyr Gly Ala Lys Gly Leu Arg Val
            505                 510                 515 aat gca cct gat gag ctg gtt tct gta ctg aag gaa gcg ctg gac tca             2120
Asn Ala Pro Asp Glu Leu Val Ser Val Leu Lys Glu Ala Leu Asp Ser
        520                 525                 530 gaa ggc ccg gtc gtg gtc gat gtc ccg gtt gat tat agc gac aac ctg             2168
Glu Gly Pro Val Val Val Asp Val Pro Val Asp Tyr Ser Asp Asn Leu
535                 540                 545                 550 gaa ctg gcg aaa aaa ctg ctg cct aac caa ttg gta taa tcacttactg              2217
Glu Leu Ala Lys Lys Leu Leu Pro Asn Gln Leu Val
                555                 560 cggcgggcag ctgctataac ttggactcag ccggcacaaa ttttttcagga tacgatagaa         2277 agaaggggtt tacc atg cgt act gct gca gaa aat caa aat aca gag caa            2327
                Met Arg Thr Ala Ala Glu Asn Gln Asn Thr Glu Gln
                                565                 570 att tta aca agc cgg acc gat gaa gta tac caa ttg tcc acg atg aca             2375
Ile Leu Thr Ser Arg Thr Asp Glu Val Tyr Gln Leu Ser Thr Met Thr
575                 580                 585                 590 tcg ctt ctt gac ggc gta tac gaa agc gac aag acg ttt gct gaa tta             2423
Ser Leu Leu Asp Gly Val Tyr Glu Ser Asp Lys Thr Phe Ala Glu Leu
            595                 600                 605 aaa aag ttc ggc gat ttc ggc atc ggc act ttc aac cat ttg gac ggg             2471
Lys Lys Phe Gly Asp Phe Gly Ile Gly Thr Phe Asn His Leu Asp Gly
        610                 615                 620 gaa ttg att gcc ttt gac aat gcg ttc tat cag ctg aag gac ggg acg             2519
Glu Leu Ile Ala Phe Asp Asn Ala Phe Tyr Gln Leu Lys Asp Gly Thr
                625                 630                 635 gca aaa cgt gta cag cct gaa gac aag tca ccg ttt tgc tcg ctt gca             2567
Ala Lys Arg Val Gln Pro Glu Asp Lys Ser Pro Phe Cys Ser Leu Ala
640                 645                 650 cat ttt tcg gag gat atc acc tat aca gct gaa ggt cct cta gca aaa             2615
His Phe Ser Glu Asp Ile Thr Tyr Thr Ala Glu Gly Pro Leu Ala Lys
655                 660                 665                 670 ccc gaa ctg gaa gac ttg atc aaa gat ctc gtc cgc agc gaa aat tta             2663
Pro Glu Leu Glu Asp Leu Ile Lys Asp Leu Val Arg Ser Glu Asn Leu
            675                 680                 685 ttt tat gcc att cgt gtg gac ggt gtt ttt aaa aaa atg aac aca aga             2711
Phe Tyr Ala Ile Arg Val Asp Gly Val Phe Lys Lys Met Asn Thr Arg
        690                 695                 700 acc gtc tcc tac cag gaa aaa ccg gtt ccc atg acg gaa gcg gtg aaa             2759
Thr Val Ser Tyr Gln Glu Lys Pro Val Pro Met Thr Glu Ala Val Lys
                705                 710                 715 tcc cag ccg gtt tac tcg ttt gaa aat aca aaa gga acg ctt gct ggt             2807
Ser Gln Pro Val Tyr Ser Phe Glu Asn Thr Lys Gly Thr Leu Ala Gly
            720                 725                 730 ttt tgg acg ccg atg ttt gca caa gga atc gcg gtc gcc ggc ttc cac             2855
Phe Trp Thr Pro Met Phe Ala Gln Gly Ile Ala Val Ala Gly Phe His
735                 740                 745                 750 ctc cat ttt att gac gac aaa cgc acc ggc ggc ggc cat gtc ttt gac             2903
Leu His Phe Ile Asp Asp Lys Arg Thr Gly Gly Gly His Val Phe Asp
                755                 760                 765 tat gtg ctt gac tac ggg acg atc cgg atc agc aaa aaa acg cat atg             2951
Tyr Val Leu Asp Tyr Gly Thr Ile Arg Ile Ser Lys Lys Thr His Met
            770                 775                 780 cat ctg gaa ctt ccg gaa aca gac gct ttt tta aat gcg aac ctt tcc             2999
His Leu Glu Leu Pro Glu Thr Asp Ala Phe Leu Asn Ala Asn Leu Ser
```

-continued

```
             785                 790                 795
cgc gcc aat ttg gca gag gaa ctg gaa aag aca gaa ggc tga           3041
Arg Ala Asn Leu Ala Glu Glu Leu Glu Lys Thr Glu Gly
    800                 805                 810 acgaaggcga agacggcccg catccggcga aaaccggatg cgggtttctt caaattgggc    3101
ggggcttgcc tgactccggc aacctaggct ttttcatctc caccccgcct gtcacttctg    3161
caatcgctta cgattatatg attcgtcaaa cgcttttccc tcaagctcag gatccagtgt    3221
cagcggctcg ttgcaatgca tgcaaatatc tacccggccc agcattttg tcggcttgcc     3281 gcagcccggg catacaa                                                   3298

<210> SEQ ID NO 3
<211> LENGTH: 3638
<212> TYPE: DNA
<213> ORGANISM: Bacillus coagulans
<220> FEATURE:
<221> NAME/KEY: exon
<222> LOCATION: (375)..(2639)
<223> OTHER INFORMATION: Open reading frame (ORF) PflB (Pyruvate formate
      lyase)
<220> FEATURE:
<221> NAME/KEY: exon
<222> LOCATION: (2729)..(3466)
<223> OTHER INFORMATION: Open reading frame (ORF) PflA (Pyruvate formate
      lyase activating enzyme)

<400> SEQUENCE: 3
ccccactcct tttatgtaac tgcttacatg aaaaatataa cgcaaacgct ttcatctggc      60
tgtgccaatt ttgtgaaata ttgagcatgt taccaaatca caactctcc ccaagaaaaa     120 taatcatgtg aaaaactgat caatttgtgt tataacacgc tttcatcgca ttttctatt     180 atatatctac ggccaaatgt tttgaacatt ctttgacaac tgctttttt ggccccaaaa     240 tgtgaacgct atcactatct ttttaaaatc gaccatgcta aaatgaaagc gtaataagaa    300
atgttcacta tttaacaaac aaacatccaa ttctgaaggc agctcattaa taggcttaaa    360
ggaggccatt taaa atg act gaa caa tta ctg aca aaa gca acg ctc tcc      410
              Met Thr Glu Gln Leu Leu Thr Lys Ala Thr Leu Ser
               1               5                   10 aaa aaa caa tgg gaa ggc ttc aaa gga gga aac tgg caa aaa gaa atc      458
Lys Lys Gln Trp Glu Gly Phe Lys Gly Gly Asn Trp Gln Lys Glu Ile
    15                  20                  25 gat gta agg gac ttt att ctg aaa aat gta acc cct tac gaa ggc gat      506
Asp Val Arg Asp Phe Ile Leu Lys Asn Val Thr Pro Tyr Glu Gly Asp
    30                  35                  40 gaa agc ttt ctt gcc ggc ccg act gaa gcc act tta aaa tta tgg gat      554
Glu Ser Phe Leu Ala Gly Pro Thr Glu Ala Thr Leu Lys Leu Trp Asp
45                  50                  55                  60 cag gtc atg gaa ctg tcg aaa cag gaa cgc gaa aaa ggc ggc gtc ctg      602
Gln Val Met Glu Leu Ser Lys Gln Glu Arg Glu Lys Gly Gly Val Leu
            65                  70                  75 gat atg gat acg aaa att gta tct acc att aca tcg cat ggc ccg ggc      650
Asp Met Asp Thr Lys Ile Val Ser Thr Ile Thr Ser His Gly Pro Gly
        80                  85                  90 tat tta aac aaa gaa ctt gaa aaa att gtc ggt ttc caa acc gat aaa      698
Tyr Leu Asn Lys Glu Leu Glu Lys Ile Val Gly Phe Gln Thr Asp Lys
        95                  100                 105 ccg ttc aaa cgt tcg atg atg ccg ttt ggc gga atc cgg atg gca gaa      746
Pro Phe Lys Arg Ser Met Met Pro Phe Gly Gly Ile Arg Met Ala Glu
    110                 115                 120 agt gcc tta aaa tct tac ggc tat gaa att gat ccg gaa atc aaa cat      794
```

```
Ser Ala Leu Lys Ser Tyr Gly Tyr Glu Ile Asp Pro Glu Ile Lys His
125                 130                 135                 140 att ttt aca gaa tgg cgg aaa acc cat aac caa ggt gta ttc gat gcc        842
Ile Phe Thr Glu Trp Arg Lys Thr His Asn Gln Gly Val Phe Asp Ala
                145                 150                 155 tac aca ccg gaa atc aaa gct gca cgg cat gcc ggc att gta aca ggc        890
Tyr Thr Pro Glu Ile Lys Ala Ala Arg His Ala Gly Ile Val Thr Gly
            160                 165                 170 ctt ccg gat gct tac ggc cgc ggc cgc att atc ggc gac tac cgg cgc        938
Leu Pro Asp Ala Tyr Gly Arg Gly Arg Ile Ile Gly Asp Tyr Arg Arg
        175                 180                 185 gtt gcc ctt tac ggt gta gat tat tta att gag caa aag aaa aaa gat        986
Val Ala Leu Tyr Gly Val Asp Tyr Leu Ile Glu Gln Lys Lys Lys Asp
    190                 195                 200 ctc gat tta atc ggc tgc ggc ttg atg aca gaa gaa gtc atc cgt gaa       1034
Leu Asp Leu Ile Gly Cys Gly Leu Met Thr Glu Glu Val Ile Arg Glu
205                 210                 215                 220 cgt gaa gaa cat tcg gaa caa att cgt gca ttg caa gaa ttg aaa caa       1082
Arg Glu Glu His Ser Glu Gln Ile Arg Ala Leu Gln Glu Leu Lys Gln
                225                 230                 235 atg gca caa agc tac gga ttc gat att tcc gaa ccg gct tca aac gca       1130
Met Ala Gln Ser Tyr Gly Phe Asp Ile Ser Glu Pro Ala Ser Asn Ala
            240                 245                 250 cac gaa gct ttc caa tgg ctg tat ttc gcg tat ctg gct gcc att aaa       1178
His Glu Ala Phe Gln Trp Leu Tyr Phe Ala Tyr Leu Ala Ala Ile Lys
        255                 260                 265 gaa caa aat ggc gcg gcc atg agt ctt ggg cgc aca tcc act ttc ctt       1226
Glu Gln Asn Gly Ala Ala Met Ser Leu Gly Arg Thr Ser Thr Phe Leu
    270                 275                 280 gac att tat att gaa aga gat ttg aaa aac ggc gtc ctg act gaa cgg       1274
Asp Ile Tyr Ile Glu Arg Asp Leu Lys Asn Gly Val Leu Thr Glu Arg
285                 290                 295                 300 gaa gca caa gaa ctc gtc gac cac ttt gtc atg aaa ctc cgc ctc gtc       1322
Glu Ala Gln Glu Leu Val Asp His Phe Val Met Lys Leu Arg Leu Val
                305                 310                 315 aaa ttt gca cgg acg gaa gac tat aat gaa ctg ttc agc ggc gac ccg       1370
Lys Phe Ala Arg Thr Glu Asp Tyr Asn Glu Leu Phe Ser Gly Asp Pro
            320                 325                 330 aca tgg gta aca gaa tcg atc ggc ggc atg gct ttg gac ggc cgt aca       1418
Thr Trp Val Thr Glu Ser Ile Gly Gly Met Ala Leu Asp Gly Arg Thr
        335                 340                 345 ctc gtt acg aaa aac tcg ttc cgc ttc ctg aac acg ctt gat aat ctc       1466
Leu Val Thr Lys Asn Ser Phe Arg Phe Leu Asn Thr Leu Asp Asn Leu
    350                 355                 360 ggc cct gcg ccg gaa ccg aac ctg acc gtg ctc tgg tcg acg aaa ctg       1514
Gly Pro Ala Pro Glu Pro Asn Leu Thr Val Leu Trp Ser Thr Lys Leu
365                 370                 375                 380 ccg gat aaa tgg aaa caa tat tgc gcg aaa atg tcg atc aag aca agc       1562
Pro Asp Lys Trp Lys Gln Tyr Cys Ala Lys Met Ser Ile Lys Thr Ser
                385                 390                 395 gcc atc caa tat gaa aac gat gac tta atg cgt gaa gaa tac ggc gat       1610
Ala Ile Gln Tyr Glu Asn Asp Asp Leu Met Arg Glu Glu Tyr Gly Asp
            400                 405                 410 gat tat ggc att gcc tgc tgt gta tcg gcg atg cgg atc ggc aaa caa       1658
Asp Tyr Gly Ile Ala Cys Cys Val Ser Ala Met Arg Ile Gly Lys Gln
        415                 420                 425 atg caa ttc ttc ggc gcc cgc gcc aac ctg gca aaa gct ttg ctg tat       1706
Met Gln Phe Phe Gly Ala Arg Ala Asn Leu Ala Lys Ala Leu Leu Tyr
    430                 435                 440
```

```
gcg att aac ggc ggc gtt gat gaa cgg tat aaa atg caa gtc gca cct    1754
Ala Ile Asn Gly Gly Val Asp Glu Arg Tyr Lys Met Gln Val Ala Pro
445             450                 455                 460 ccg ttc cag ccg atc aca tcg gaa tat ctc gat tac gat gaa gtc atg    1802
Pro Phe Gln Pro Ile Thr Ser Glu Tyr Leu Asp Tyr Asp Glu Val Met
                465                 470                 475 gaa aaa tac gat cgg atg cta gac tgg ctt gca ggc gtt tat atc aat    1850
Glu Lys Tyr Asp Arg Met Leu Asp Trp Leu Ala Gly Val Tyr Ile Asn
            480                 485                 490 gct ttg aac atc att cat tat atg cat gac aaa tac agc tac gaa cgg    1898
Ala Leu Asn Ile Ile His Tyr Met His Asp Lys Tyr Ser Tyr Glu Arg
        495                 500                 505 ctt gaa atg gca ttg cat gac cgc aat gta ctg cgc acg atg gct tgc    1946
Leu Glu Met Ala Leu His Asp Arg Asn Val Leu Arg Thr Met Ala Cys
    510                 515                 520 ggc gtt gcc ggc ttg tct gtt gcg gcc gac tct cta agc gcc atc aaa    1994
Gly Val Ala Gly Leu Ser Val Ala Ala Asp Ser Leu Ser Ala Ile Lys
525                 530                 535                 540 tat gcg aaa gta aaa gtc atc cgt gac gaa gac ggc ctt gct gtt gac    2042
Tyr Ala Lys Val Lys Val Ile Arg Asp Glu Asp Gly Leu Ala Val Asp
                545                 550                 555 tat gaa gtc gaa ggc gat tac ccg aaa tac ggc aac aac gat gac cgc    2090
Tyr Glu Val Glu Gly Asp Tyr Pro Lys Tyr Gly Asn Asn Asp Asp Arg
            560                 565                 570 gtc gac caa att gcc gtc aat ctc gtc aag tcg ttt atg caa aaa ctg    2138
Val Asp Gln Ile Ala Val Asn Leu Val Lys Ser Phe Met Gln Lys Leu
        575                 580                 585 caa aaa tat ccg act tac cgg aac gct gtc cat act tct tcg atc ctg    2186
Gln Lys Tyr Pro Thr Tyr Arg Asn Ala Val His Thr Ser Ser Ile Leu
    590                 595                 600 aca att aca tcg aac gtt gta tac ggc aag aaa aca gga agc aca ccg    2234
Thr Ile Thr Ser Asn Val Val Tyr Gly Lys Lys Thr Gly Ser Thr Pro
605                 610                 615                 620 gac ggc cgg aaa gca ggc gaa ccg ttc gcc cct ggc gca aac ccg atg    2282
Asp Gly Arg Lys Ala Gly Glu Pro Phe Ala Pro Gly Ala Asn Pro Met
                625                 630                 635 cac ggc cgc gat tcg cac ggc gca gtc gca tcg ttg aca tct gtt gcg    2330
His Gly Arg Asp Ser His Gly Ala Val Ala Ser Leu Thr Ser Val Ala
            640                 645                 650 aaa ctg cct tat aaa tat tcg ctt gac ggc att tcc aac act ttc tcg    2378
Lys Leu Pro Tyr Lys Tyr Ser Leu Asp Gly Ile Ser Asn Thr Phe Ser
        655                 660                 665 att gtc ccg gaa gcg ctc gga cac gaa gaa gaa aca cag gtc tcc aac    2426
Ile Val Pro Glu Ala Leu Gly His Glu Glu Glu Thr Gln Val Ser Asn
    670                 675                 680 ctg gac ggc atg ctg gac ggc tat atg gcg aaa aaa gcg cac cac tta    2474
Leu Asp Gly Met Leu Asp Gly Tyr Met Ala Lys Lys Ala His His Leu
685                 690                 695                 700 aac gtc aac gtc ctg cat cgc gaa aca ttg ctg gat gcg atg gat cat    2522
Asn Val Asn Val Leu His Arg Glu Thr Leu Leu Asp Ala Met Asp His
                705                 710                 715 ccg gaa aaa tat ccg caa ttg acg atc cgt gta tcg gga tat gcg gta    2570
Pro Glu Lys Tyr Pro Gln Leu Thr Ile Arg Val Ser Gly Tyr Ala Val
            720                 725                 730 aac ttc att aaa ttg aca agg gaa caa caa ctt gaa gtc att aac cgc    2618
Asn Phe Ile Lys Leu Thr Arg Glu Gln Gln Leu Glu Val Ile Asn Arg
        735                 740                 745 acg ttc cat gaa atg atg taa actgattcgg gcggcatgca cctgcgtgcc       2669
Thr Phe His Glu Met Met
        750
```

```
                                                    -continued ccctcccccc tattaaacac ttaacttatg gggaatctat atagaaggat ttgattgag   2728 atg aac atg aca acg cgc att cat tcc act gaa tcg ttt ggc aca gtc   2776
Met Asn Met Thr Thr Arg Ile His Ser Thr Glu Ser Phe Gly Thr Val
755                 760                 765                 770 gac ggg ccc ggc atc cgc tat gtc gta ttt acg caa ggc tgc ccg ctg   2824
Asp Gly Pro Gly Ile Arg Tyr Val Val Phe Thr Gln Gly Cys Pro Leu
                775                 780                 785 cgc tgc aaa ttc tgc cac aac cca gat aca tgg aaa atc aat gaa ggc   2872
Arg Cys Lys Phe Cys His Asn Pro Asp Thr Trp Lys Ile Asn Glu Gly
            790                 795                 800 aat gaa atg agc gtc gaa gag att atg agc gat gtg cgc gat tac ctg   2920
Asn Glu Met Ser Val Glu Glu Ile Met Ser Asp Val Arg Asp Tyr Leu
        805                 810                 815 cct ttt att gaa gct tcc ggc ggt ggc att aca gtg agc ggc ggt gaa   2968
Pro Phe Ile Glu Ala Ser Gly Gly Gly Ile Thr Val Ser Gly Gly Glu
    820                 825                 830 ccg ctt ttg cac ctc gat ttt ctg atc gaa ttg ttt aaa gcg tgc aaa   3016
Pro Leu Leu His Leu Asp Phe Leu Ile Glu Leu Phe Lys Ala Cys Lys
835                 840                 845                 850 gaa att ggc gtc cat act gcc att gac aca gcg ggc gga tgt ttc tcg   3064
Glu Ile Gly Val His Thr Ala Ile Asp Thr Ala Gly Gly Cys Phe Ser
                855                 860                 865 cgc agt tcc cgg ttt atg gaa aaa ctg gat gaa ttg atg aaa tat aca   3112
Arg Ser Ser Arg Phe Met Glu Lys Leu Asp Glu Leu Met Lys Tyr Thr
            870                 875                 880 aat ctt gta tta ttg gac atc aag cat att gac ccg gaa aag cat aaa   3160
Asn Leu Val Leu Leu Asp Ile Lys His Ile Asp Pro Glu Lys His Lys
        885                 890                 895 tgg ctg acc ggc atg tca aat gag cat att ctc gat ttc gcc cgg tat   3208
Trp Leu Thr Gly Met Ser Asn Glu His Ile Leu Asp Phe Ala Arg Tyr
    900                 905                 910 ctc gct gac aag cat att ccg gtc tgg atc cgc cat gtg ctc gtt ccc   3256
Leu Ala Asp Lys His Ile Pro Val Trp Ile Arg His Val Leu Val Pro
915                 920                 925                 930 ggc gtc gat tca gaa gaa gat ttg caa aaa aca tct gat ttt atc cat   3304
Gly Val Asp Ser Glu Glu Asp Leu Gln Lys Thr Ser Asp Phe Ile His
                935                 940                 945 tcg ctg cca aac gtc gaa aaa atc gaa atc ctt ccg tac cat aag tta   3352
Ser Leu Pro Asn Val Glu Lys Ile Glu Ile Leu Pro Tyr His Lys Leu
            950                 955                 960 ggc gtc tac aaa tac gag gcg ctc ggc atc gac tat ccc ctc aaa ggt   3400
Gly Val Tyr Lys Tyr Glu Ala Leu Gly Ile Asp Tyr Pro Leu Lys Gly
        965                 970                 975 gtc gaa ccg ccg aca aaa gaa caa gtt gca cat gcg gaa cag att tta   3448
Val Glu Pro Pro Thr Lys Glu Gln Val Ala His Ala Glu Gln Ile Leu
    980                 985                 990 aaa agg gaa ttg cag taa agaaaaagcg ccggctgtcc gccggcactt          3496
Lys Arg Glu Leu Gln
995 ttttattccg cctaaaagaa cgatacaatg ttaagaaagc ggaaaaactt agagctcctc   3556 tccccctgaaa aattgccccg ggttttttta tccttttgct ggtaacgcgt catacggcaa   3616 gataaacggc aaaatggtcg cc                                          3638

<210> SEQ ID NO 4
<211> LENGTH: 29
<212> TYPE: DNA
<213> ORGANISM: Artificial Sequence
<220> FEATURE:
```

<223> OTHER INFORMATION: Primer9

<400> SEQUENCE: 4
ccctacgtat tggaacgggt gcagttggt                                29

<210> SEQ ID NO 5
<211> LENGTH: 29
<212> TYPE: DNA
<213> ORGANISM: Artificial Sequence
<220> FEATURE:
<223> OTHER INFORMATION: Primer10

<400> SEQUENCE: 5
cccgaattcc cgggttgctg gcaacaaga                                29

<210> SEQ ID NO 6
<211> LENGTH: 29
<212> TYPE: DNA
<213> ORGANISM: Artificial Sequence
<220> FEATURE:
<223> OTHER INFORMATION: Primer11

<400> SEQUENCE: 6
cccgaattct ttgagcgccc aatttggaa                                29

<210> SEQ ID NO 7
<211> LENGTH: 29
<212> TYPE: DNA
<213> ORGANISM: Artificial Sequence
<220> FEATURE:
<223> OTHER INFORMATION: Primer12

<400> SEQUENCE: 7
cccaggcctc cggaacgcca acgtacaca                                29

<210> SEQ ID NO 8
<211> LENGTH: 20
<212> TYPE: DNA
<213> ORGANISM: Artificial Sequence
<220> FEATURE:
<223> OTHER INFORMATION: Primer17

<400> SEQUENCE: 8
acgagccgct gacactggat                                          20

<210> SEQ ID NO 9
<211> LENGTH: 20
<212> TYPE: DNA
<213> ORGANISM: Artificial Sequence
<220> FEATURE:
<223> OTHER INFORMATION: Primer18

<400> SEQUENCE: 9
gccgtcttcg ccttcgttca                                          20

<210> SEQ ID NO 10
<211> LENGTH: 20
<212> TYPE: DNA
<213> ORGANISM: Artificial Sequence
<220> FEATURE:
<223> OTHER INFORMATION: Primer19

<400> SEQUENCE: 10
tgaaccgaac cgcctgctgt                                          20

```
<210> SEQ ID NO 11
<211> LENGTH: 20
<212> TYPE: DNA
<213> ORGANISM: Artificial Sequence
<220> FEATURE:
<223> OTHER INFORMATION: Primer20

<400> SEQUENCE: 11
tcgcgccaga cgatatgcac                                              20

<210> SEQ ID NO 12
<211> LENGTH: 20
<212> TYPE: DNA
<213> ORGANISM: Artificial Sequence
<220> FEATURE:
<223> OTHER INFORMATION: Primer21

<400> SEQUENCE: 12
tgtcataagt cgccgaaccg                                              20

<210> SEQ ID NO 13
<211> LENGTH: 20
<212> TYPE: DNA
<213> ORGANISM: Artificial Sequence
<220> FEATURE:
<223> OTHER INFORMATION: Primer22

<400> SEQUENCE: 13
tgattgtatg ccgccacgaa                                              20

<210> SEQ ID NO 14
<211> LENGTH: 20
<212> TYPE: DNA
<213> ORGANISM: Artificial Sequence
<220> FEATURE:
<223> OTHER INFORMATION: Primer23

<400> SEQUENCE: 14
ggtgttgcag aagagcttgt                                              20

<210> SEQ ID NO 15
<211> LENGTH: 20
<212> TYPE: DNA
<213> ORGANISM: Artificial Sequence
<220> FEATURE:
<223> OTHER INFORMATION: Primer24

<400> SEQUENCE: 15
gtgccgcaat cggaataatc                                              20

<210> SEQ ID NO 16
<211> LENGTH: 20
<212> TYPE: DNA
<213> ORGANISM: Artificial Sequence
<220> FEATURE:
<223> OTHER INFORMATION: Primer25

<400> SEQUENCE: 16
catcaacgcc gccgttaatc                                              20

<210> SEQ ID NO 17
<211> LENGTH: 20
<212> TYPE: DNA
<213> ORGANISM: Artificial Sequence
<220> FEATURE:
<223> OTHER INFORMATION: Primer26
```

```
<400> SEQUENCE: 17
tcgttccgct tcctgaacac                                                  20

<210> SEQ ID NO 18
<211> LENGTH: 20
<212> TYPE: DNA
<213> ORGANISM: Artificial Sequence
<220> FEATURE:
<223> OTHER INFORMATION: Primer27

<400> SEQUENCE: 18
cccgccgcaa atcattatcg                                                  20

<210> SEQ ID NO 19
<211> LENGTH: 19
<212> TYPE: DNA
<213> ORGANISM: Artificial Sequence
<220> FEATURE:
<223> OTHER INFORMATION: Primer28

<400> SEQUENCE: 19
taaaagcacc cgcaaagtt                                                   19

<210> SEQ ID NO 20
<211> LENGTH: 20
<212> TYPE: DNA
<213> ORGANISM: Artificial Sequence
<220> FEATURE:
<223> OTHER INFORMATION: Primer29

<400> SEQUENCE: 20
agatcttaag ccgtgtggag                                                  20

<210> SEQ ID NO 21
<211> LENGTH: 20
<212> TYPE: DNA
<213> ORGANISM: Artificial Sequence
<220> FEATURE:
<223> OTHER INFORMATION: Primer30

<400> SEQUENCE: 21
cgcaacaata ctgccgattc                                                  20

<210> SEQ ID NO 22
<211> LENGTH: 20
<212> TYPE: DNA
<213> ORGANISM: Artificial Sequence
<220> FEATURE:
<223> OTHER INFORMATION: Primer31

<400> SEQUENCE: 22
tcgcttccgc tcgtcgtctt                                                  20

<210> SEQ ID NO 23
<211> LENGTH: 20
<212> TYPE: DNA
<213> ORGANISM: Artificial Sequence
<220> FEATURE:
<223> OTHER INFORMATION: Primer32

<400> SEQUENCE: 23
tcccgcaaat cccttacctg                                                  20

<210> SEQ ID NO 24
<211> LENGTH: 20
```

```
<212> TYPE: DNA
<213> ORGANISM: Artificial Sequence
<220> FEATURE:
<223> OTHER INFORMATION: Primer33

<400> SEQUENCE: 24
ttggaggcga acaaagaaca                                            20

<210> SEQ ID NO 25
<211> LENGTH: 20
<212> TYPE: DNA
<213> ORGANISM: Artificial Sequence
<220> FEATURE:
<223> OTHER INFORMATION: Primer34

<400> SEQUENCE: 25
cggcaatgga aaaagaaatg                                            20
```